(12) United States Patent
Kikuchi et al.

(10) Patent No.: US 10,550,120 B2
(45) Date of Patent: Feb. 4, 2020

(54) INDOLE ALKALOID COMPOUND HAVING IMMUNE CHECKPOINT INHIBITORY ACTION

(71) Applicants: TOHOKU UNIVERSITY, Sendai-shi, Miyagi (JP); FUSO PHARMACEUTICAL INDUSTRIES, LTD., Osaka-shi, Osaka (JP)

(72) Inventors: Haruhisa Kikuchi, Sendai (JP); Yoshiteru Oshima, Sendai (JP); Toshio Hattori, Takahashi (JP); Osamu Yamada, Osaka (JP); Jing Zhang, Osaka (JP); Shinya Kida, Osaka (JP); Shinya Murase, Osaka (JP)

(73) Assignees: TOHOKU UNIVERSITY, Miyagi (JP); FUSO PHARMACEUTICAL INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/087,947

(22) PCT Filed: Mar. 24, 2017

(86) PCT No.: PCT/JP2017/012157
§ 371 (c)(1),
(2) Date: Sep. 24, 2018

(87) PCT Pub. No.: WO2017/164407
PCT Pub. Date: Sep. 28, 2017

(65) Prior Publication Data
US 2019/0092774 A1    Mar. 28, 2019

(30) Foreign Application Priority Data
Mar. 25, 2016 (JP) ................. 2016-062267

(51) Int. Cl.
| | |
|---|---|
| *C07D 471/14* | (2006.01) |
| *C07D 401/06* | (2006.01) |
| *C07D 491/052* | (2006.01) |
| *A61K 39/39* | (2006.01) |
| *A61P 37/06* | (2006.01) |
| *A61K 39/00* | (2006.01) |

(52) U.S. Cl.
CPC ............ *C07D 471/14* (2013.01); *A61K 39/39* (2013.01); *A61P 37/06* (2018.01); *C07D 401/06* (2013.01); *C07D 491/052* (2013.01); *A61K 2039/55511* (2013.01)

(58) Field of Classification Search
CPC ............... C07D 471/14; C07D 401/06; C07D 491/052; A61K 37/06; A61K 39/39
See application file for complete search history.

(56) References Cited

FOREIGN PATENT DOCUMENTS

| CN | 101406701 A | 4/2009 |
|---|---|---|
| JP | 2009503045 A | 1/2009 |
| WO | 2007017643 A1 | 2/2007 |
| WO | 2009029206 A1 | 3/2009 |

OTHER PUBLICATIONS

Baxter, J am Chem Soc, vol. 112, 7682-7692, 1990. (Year: 1990).*
Tixidre, Serie C: Sciences Chimiques, vol. 288, 57-60, 1979. (Year: 1979).*
Kocsis, Biodiversity, 375-377, 2002. (Year: 2002).*
Grosso JF & Kunkel NJ, Cancer Immunity vol. 13:p. 5 (Jan. 22, 2013), 14 pages provided.
Pardoll D.M Nature Reviews Cancer 12: 252-264 (Apr. 2012), 13 pages provided.
Adams J et al., Nature Review, vol. 14: 603-621 (Sep. 2015), 19 pages provided.
Sky Ng TH et al., Frontiers in Immunology, vol. 4: 1-13 (May 2013), 13 pages provided.
Itakura E et al., Modern Pathology, vol. 24: 801-809 (2011), 9 pages provided.
Tixidre, Arlette et al., Serie C: Sciences Chimiques, vol. 288, pp. 57-60 (1979), 6 pages provided.
Database registry No. 1809495-50-8, 1809490-11-6, 1809476-35-4; 3 pages provided.
Kocsis, Akos et al., Biodiversity, pp. 375-377 (2002), 3 pages provided.
Baxter, Ellen W. et al., Journal of the American Chemical Society, vol. 112, pp. 7682-7692 (1990), 11 pages provided.
Wenkert et al., Journal of the American Chemical Society, vol. 87, pp. 5461-5467 (1965), 7 pages provided.
Kikuchi et al., Organic Letters, vol. 18, pp. 5948-5951 (2016), 4 pages provided.

(Continued)

*Primary Examiner* — D Margaret M Seaman
(74) *Attorney, Agent, or Firm* — Hamre, Schumann, Mueller & Larson, P.C.

(57) ABSTRACT

The present invention provides a medicament useful for treatment and/or prevention of cancer, a vaccine adjuvant, and an inhibitor of immune checkpoint comprising a compound of formula (I):

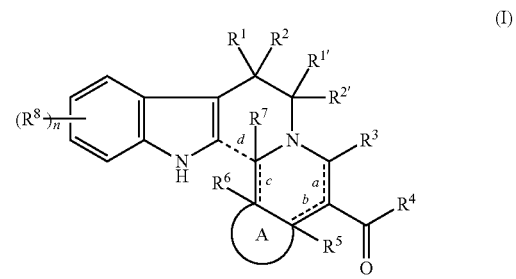

or a pharmaceutically acceptable salt thereof, wherein Bonds a-d, Ring A, $R^1$, $R^{1'}$, $R^2$, $R^{2'}$, $R^3$-$R^8$, and n are as defined in the present specification.

18 Claims, 1 Drawing Sheet

(56) References Cited

OTHER PUBLICATIONS

International Search Report issued in PCT/JP2017/012157, dated Jun. 27, 2017.
Written Opinion issued in PCT/JP2017/012157, dated Jun. 27, 2017.

* cited by examiner

INDOLE ALKALOID COMPOUND HAVING IMMUNE CHECKPOINT INHIBITORY ACTION

TECHNICAL FIELD

The present invention relates to a novel indole alkaloid compound, especially an indole alkaloid compound having immune checkpoint inhibitory effect. The present invention may also be useful for prevention and/or treatment of diseases caused by immune checkpoint, including cancer.

BACKGROUND ART

Although organisms have immune systems to protect themselves from cancer cells arising from their own bodies, the immune systems often decline in their function and do not work on cancer cells once cancer progresses. Recently, it has been revealed that cancer cells have some functions to evade the immune systems of organisms. One of the functions is that cancer cells produce cytokine such as IL-10 and TGF-β, which induces naive T cells to inducible regulatory T cells (iTregs). Against cancer cells, the cellular immunity in which killer T cells play a central role is important means. Once iTregs which effect on immunosuppression are increased, however, CTLA-4 (cytotoxic T-lymphocyte-associated protein 4) which is expressed on the surface of cell membrane reduces the number of killer T cells, which makes impossible to kill cancer cells. CTLA-4 molecule is a member of immunoglobulin superfamily which is expressed on the surface of a regulatory T cell, and inherently CTLA-4 molecule works as a negative feedback control factor when dendritic cells or macrophages provide T cells with an antigen presentation, and controls these cells (Non-Patent Literature 1).

Methods for treating cancer are mainly surgical, chemical, and radiation therapies, but there have not been any established treatment methods which can bring in some sufficient effect yet, thus is desired to establish a novel method for the treatment. The molecule which inhibitively acts on immunity, such as CTLA-4 is referred to as "immune checkpoint", and CTLA-4 has been a new target for treating cancer as one of the immune checkpoint (Non-Patent Literature 2 and 3). In addition, IL-10 which is produced from various immunocompetent cells also inhibitively acts on immune systems, and it is known that cancer cells also produce IL-10 (Non-Patent Literature 4 and 5). Thus, it is expected that cancer can be treated by inhibiting CTLA-4 expression in regulatory T cells (Tregs) and/or immunosuppressive cytokine IL-10 production, and therefore, compounds which have such function has attracted attention as a novel cancer treatment.

Anti-CTLA-4 antibody (ipilimumab), anti-PD-1 antibody (nivolumab, pembrolizumab) and anti-PD-L1 antibody (MPDL3280A, MEDI4736) have already been developed as inhibitors of immune checkpoint which target CTLA-4 and PD-1 (or PD-L1) so far, but these medicines are antibody drugs and no small molecule as an inhibitor of immune checkpoint has discovered yet.

PRIOR ART

Non-Patent Reference

[Non-Patent Literature 1] Grosso J F & Kunkel N J, Cancer Immunity 13:p. 5 (2013)
[Non-Patent Literature 2] Pardoll D. M Nature Reviews Cancer 12: 252-264 (2012)
[Non-Patent Literature 3] Adams J et al., Nature Review 14: 603-621 (2015)
[Non-Patent Literature 4] Sky Ng T H et al., Frontiers in Immunology 4: 1-13 (2013)
[Non-Patent Literature 5] Itakura E et al., Modern Pathol 24: 801-809 (2011)

SUMMARY OF INVENTION

Technical Problem

An object of the present invention is to study for searching a small molecule which has inhibitory effect on CTLA-4 expression and/or IL-10 production and to provide a medicament and a vaccine adjuvant useful for treating disease caused by immune checkpoint, such as cancer.

Solution to Problem

The present inventors have extensively studied to find that a group of compounds represented by the following formula (I) which are extracted and purified from plants such as accessory fruits of *Cornus* fruits, *Gardenia* fruits, and *Swertia* herbs has inhibitory effect on CTLA-4 expression and IL-10 production. The present invention provides an indole alkaloid compound of the following formula (I) and a pharmaceutically acceptable salt thereof (hereinafter, it may be referred to as the "compound of the present invention"), and medical use based on their inhibitory effect on immune checkpoint.

The present invention provides the following embodiments of the invention.

[1] A compound of formula (I):

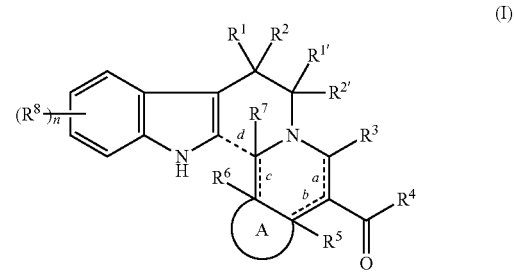

or a pharmaceutically acceptable salt thereof
wherein
Bonds a-c: ==== denote a single bond or a double bond, and Bond d: - - - - denotes absent or a single bond, provided that when Bond a is a double bond, Bond b is a single bond; when Bond b is a double bond, Bond a is a single bond and $R^5$ is absent; when Bond c is a double bond, $R^6$ is absent; and when Bond c is a double bond and Bond d is a single bond, $R^6$ and $R^7$ are absent;

Ring A is $C_{3-6}$ cycloalkyl ring, $C_{3-6}$ cycloalkenyl ring, or 5- or 6-membered monocyclic heterocycle, wherein the cycloalkyl ring, cycloalkenyl ring and monocyclic heterocycle may be substituted with one or more the same or different groups selected from the group consisting of halogen, hydroxy, oxo, amino, nitro, mono- or di-$C_{1-6}$ alkylamino, $C_{1-4}$ acyl, $C_{1-6}$ alkyl, $C_{1-6}$ haloalkyl, $C_{1-6}$ hydroxyalkyl, $C_{1-6}$ alkoxy, and $C_{1-6}$ haloalkoxy, at any substitutable position;

$R^1$, $R^{1'}$, $R^2$, $R^{2'}$, and $R^3$ are independently hydrogen, halogen, hydroxy, amino, nitro, mono- or di-$C_{1-6}$ alkylamino, $C_{1-6}$ alkyl, $C_{1-6}$ haloalkyl, $C_{1-6}$ hydroxyalkyl, $C_{1-6}$ alkoxy, or $C_{1-6}$ haloalkoxy;

$R^4$ is hydrogen, halogen, hydroxy, amino, mono- or di-$C_{1-6}$ alkyl-amino, $C_{1-5}$ alkyl, $C_{2-6}$ alkenyl, $C_{2-6}$ alkynyl, $C_{1-6}$ alkoxy, $C_{3-6}$ cycloalkyl, 3- to 6-membered heterocycloalkyl, $C_{6-10}$ aryl, or 6- to 10-membered heteroaryl, wherein the alkyl, alkenyl, alkynyl, alkoxy, cycloalkyl, heterocycloalkyl, aryl, and heteroaryl may be independently substituted with one or more the same or different groups selected from the group consisting of halogen, hydroxy, amino, nitro, mono- or di-$C_{1-6}$ alkylamino, $C_{1-4}$ acyl, $C_{1-6}$ alkyl, $C_{1-6}$ haloalkyl, $C_{1-6}$ hydroxyalkyl, $C_{1-6}$ alkoxy, and $C_{1-6}$ haloalkoxy, at any substitutable position;

$R^5$, $R^6$, and $R^7$ are independently hydrogen, halogen, hydroxy, $C_{1-3}$ alkyl, $C_{1-3}$ haloalkyl, $C_{1-3}$ hydroxyalkyl, $C_{1-3}$ alkoxy, or $C_{1-3}$ haloalkoxy;

$R^8$ is independently hydrogen, halogen, hydroxy, amino, nitro, mono- or di-$C_{1-6}$ alkyl-amino, $C_{1-6}$ alkyl, $C_{2-6}$ alkenyl, $C_{2-6}$ alkynyl, $C_{1-6}$ alkoxy, benzyloxy, $C_{3-6}$ cycloalkyl, 3- to 6-membered heterocycloalkyl, $C_{6-10}$ aryl, or 6- to 10-membered heteroaryl, wherein the alkyl, alkenyl, alkynyl, alkoxy, cycloalkyl, heterocycloalkyl, aryl, and heteroaryl may be independently substituted with one or more the same or different groups selected from the group consisting of halogen, hydroxy, amino, mono- or di-$C_{1-6}$ alkyl-amino, $C_{1-4}$ acyl, $C_{1-6}$ alkyl, $C_{1-6}$ haloalkyl, $C_{1-6}$ hydroxyalkyl, $C_{1-6}$ alkoxy, and $C_{1-6}$ haloalkoxy, at any substitutable position; and n is 1-4.

[2] The compound of [1] or a pharmaceutically acceptable salt thereof, provided that the compound in which Bond a denotes a double bond and $R^8$ is hydrogen is excluded.

[3] The compound of [1] or a pharmaceutically acceptable salt thereof, provided that the compound in which Bond a denotes a double bond is excluded.

[4] The compound of [1] or a pharmaceutically acceptable salt thereof, provided that the following compounds are excluded:

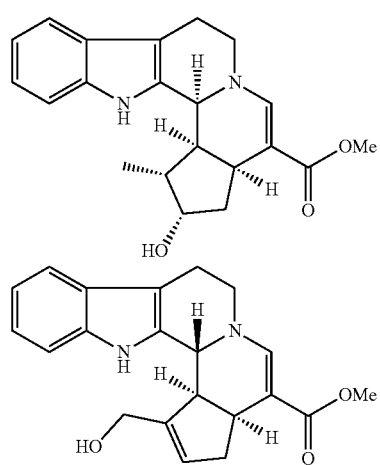

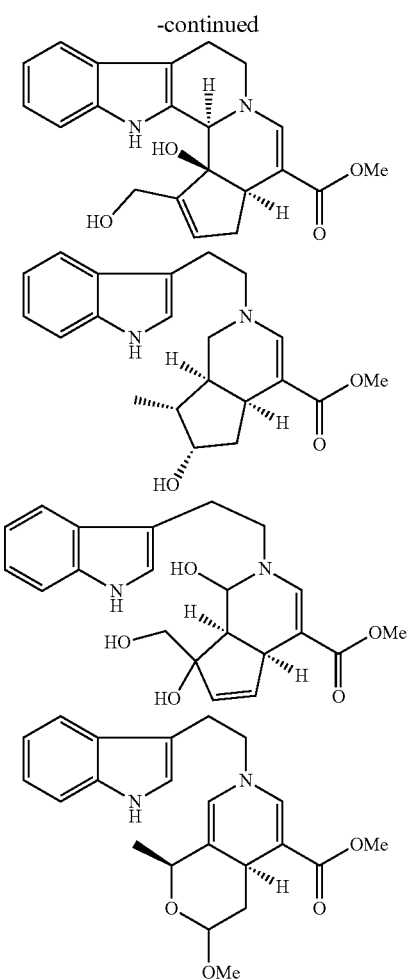

[5] The compound of any one of [1]-[4] or a pharmaceutically acceptable salt thereof, wherein $R^4$ is hydrogen, hydroxy, amino, mono- or di-$C_{1-6}$ alkyl-amino, $C_{1-6}$ alkyl, $C_{1-6}$ haloalkyl, $C_{1-6}$ hydroxyalkyl, $C_{1-6}$ alkoxy, or $C_{1-6}$ haloalkoxy.

[6] The compound of any one of [1]-[5] or a pharmaceutically acceptable salt thereof, wherein $R^8$ is independently hydrogen, halogen, hydroxy, amino, mono- or di-$C_{1-6}$ alkyl-amino, $C_{1-6}$ alkyl, $C_{1-6}$ haloalkyl, $C_{1-6}$ hydroxyalkyl, $C_{1-6}$ alkoxy, benzyloxy, or $C_{1-6}$ haloalkoxy.

[7] The compound of any one of [1]-[6] or a pharmaceutically acceptable salt thereof, wherein Ring A is $C_{5-6}$ cycloalkyl ring, $C_{5-6}$ cycloalkenyl ring, or 5- or 6-membered saturated monocyclic heterocycle, wherein the cycloalkyl ring, cycloalkenyl ring, and saturated monocyclic heterocycle may be independently substituted with one or more the same or different groups selected from the group consisting of hydroxy, oxo, $C_{1-6}$ alkyl, $C_{1-6}$ haloalkyl, $C_{1-6}$ hydroxyalkyl, $C_{1-6}$ alkoxy, and $C_{1-6}$ haloalkoxy, at any substitutable position.

[8] The compound of any one of [1]-[7] or a pharmaceutically acceptable salt thereof, wherein Ring A is selected from the group consisting of the following groups:

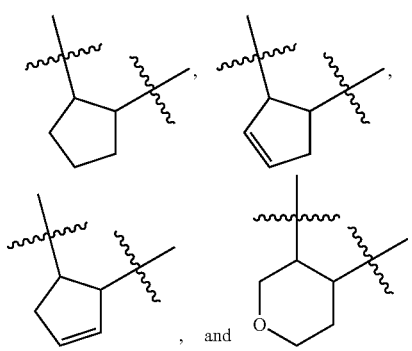

, and which are independently substituted with one or more the same or different groups selected from the group consisting of hydroxy, oxo, $C_{1-3}$ alkyl, $C_{1-3}$ hydroxyalkyl, and $C_{1-3}$ alkoxy, at any substitutable position.

[9] The compound of any one of [1]-[8] or a pharmaceutically acceptable salt thereof, wherein and $R^7$ are independently hydrogen or hydroxy.

[10] The compound of any one of [1]-[9] or a pharmaceutically acceptable salt thereof, wherein $R^1$, $R^{1'}$, $R^2$, $R^{2'}$ and $R^8$ are hydrogen.

[11] The compound of any one of [1]-[10] or a pharmaceutically acceptable salt thereof, wherein $R^3$ is $C_{1-6}$ alkyl, $C_{1-6}$ haloalkyl, $C_{1-6}$ hydroxyalkyl, $C_{1-6}$ alkoxy, or $C_{1-6}$ haloalkoxy.

[12] The compound of any one of [1]-[11] or a pharmaceutically acceptable salt thereof, wherein the compound is

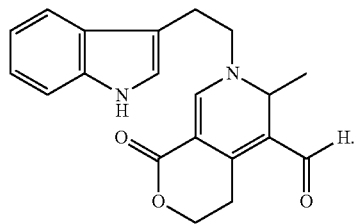

[13] A pharmaceutical composition comprising the compound of any one of [1]-[12] or a pharmaceutically acceptable salt thereof.

[14] A medicament for treating cancer, which comprises the compound of any one of [1]-[12] or a pharmaceutically acceptable salt thereof as an active ingredient.

[15] The medicament of [14], wherein the cancer is malignant melanoma, glioblastoma, lung cancer, gastric cancer, colorectal cancer, liver cancer, pancreatic cancer, renal cancer, adrenal cancer, biliary tract cancer, esophageal cancer, pharyngeal cancer, laryngeal cancer, oral cancer, bladder cancer, tongue cancer, thyroid cancer, skin cancer, breast cancer, prostate cancer, testicular cancer, uterine cancer, cervical cancer, ovarian cancer, osteosarcoma, chondrosarcoma, rhabdomyosarcoma, leiomyosarcoma, leukemia including adult T-cell leukemia, malignant lymphoma, or multiple myeloma.

[16] An inhibitor of immune checkpoint comprising the compound of any one of [1]-[12] or a pharmaceutically acceptable salt thereof as an active ingredient.

[17] The inhibitor of [16], wherein the immune checkpoint is CTLA-4.

[18] A vaccine adjuvant comprising the compound of any one of [1]-[12] or a pharmaceutically acceptable salt thereof.

[19] A method for treating cancer comprising administrating a therapeutically effective amount of the compound of any one of [1]-[12] or a pharmaceutically acceptable salt thereof to a patient in need thereof.

[20] The compound of any one of [1]-[12] or a pharmaceutically acceptable salt thereof, which is used for treating cancer.

[21] Use of the compound of any one of [1]-[12] or a pharmaceutically acceptable salt thereof in the manufacture of a medicament for cancer.

[22] A method for inhibiting immune checkpoint comprising administrating a therapeutically acceptable amount of the compound of any one of [1]-[12] or a pharmaceutically acceptable salt thereof to a patient in need thereof.

Effect of Invention

The compound of the present invention has the CTLA-4 expression inhibitory effect and the IL-10 production inhibitory effect, and is useful as a novel medicament for treating and/or preventing diseases caused by immune checkpoint, especially cancer (for example, malignant melanoma, glioblastoma, lung cancer, gastric cancer, colorectal cancer, liver cancer, pancreatic cancer, renal cancer, adrenal cancer, biliary tract cancer, esophageal cancer, pharyngeal cancer, laryngeal cancer, oral cancer, bladder cancer, tongue cancer, thyroid cancer, skin cancer, breast cancer, prostate cancer, testicular cancer, uterine cancer, cervical cancer, ovarian cancer, osteosarcoma, chondrosarcoma, rhabdomyosarcoma, leiomyosarcoma, leukemia comprising adult T-cell leukemia, malignant lymphoma, multiple myeloma). In addition, it is also useful as a vaccine adjuvant due to its inhibitory activity on immune checkpoint.

DESCRIPTION OF EMBODIMENTS

Figure 1:
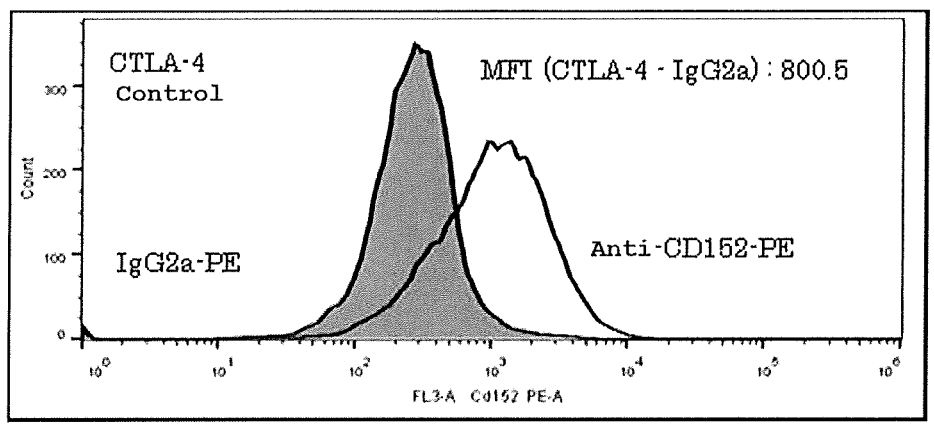
FIG. 1 shows results (histgrams) of FCM analysis of MT2 cells colored with anti-CTLA4 (CD152)-PE antibody or IgG1-PE antibody as an isotype control.
Figure 2:
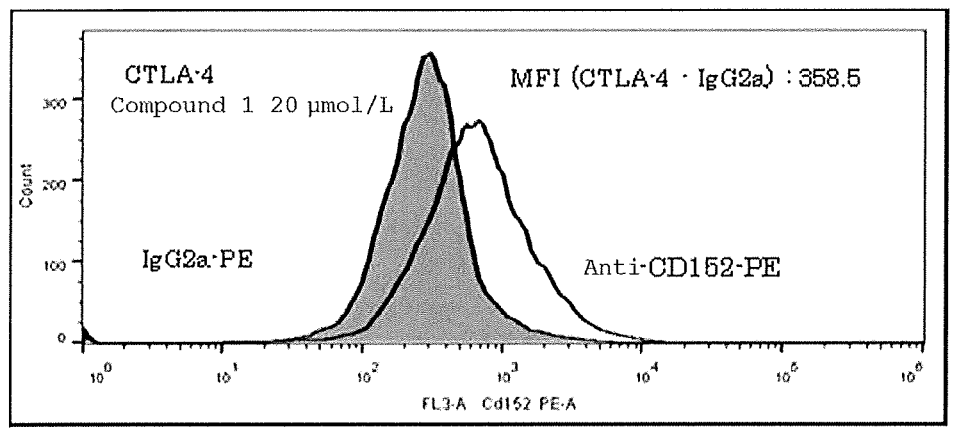
FIG. 2 shows results (histgrams) of FCM analysis of MT2 cells colored with anti-CTLA4 (CD152)-PE antibody or IgG1-PE antibody as an isotype control.

Each term in the present specification is defined below.

The term "$C_{1-6}$ alkyl" means a linear or branched-chain saturated carbohydrate having 1-6 carbon atoms, which may be optionally substituted with one or more substituents defined in the present invention. Preferably, the "$C_{1-6}$ alkyl" may have 1-5, 1-4, or 1-3 carbon atoms. Such examples include methyl, ethyl, propyl, isopropyl, but 1, isobutyl, sec-butyl, tert-butyl, pentyl, isopentyl, neopentyl, and hexyl.

The term "$C_{2-6}$ alkenyl" means a linear or branched-chain aliphatic carbohydrate having 2-6 carbon atoms and one or more carbon-carbon double bonds, which may be optionally substituted with one or more substituents defined in the present invention. Preferably, the "$C_{2-6}$ alkenyl" may have 2-5, 2-4, or 2-3 carbon atoms. Such examples include ethenyl, propenyl, butenyl, pentenyl, and hexynyl.

The term "$C_{2-6}$ alkynyl" means a linear or branched-chain aliphatic carbohydrate having 2-6 carbon atoms and one or more carbon-carbon triple bonds, which may be optionally substituted with one or more substituents defined in the present invention. Preferably, the "$C_{2-6}$ alkynyl" may have 2-5, 2-4, or 2-3 carbon atoms. Such examples include ethynyl, propynyl, butynyl, pentynyl, and hexynyl.

The term "$C_{3-6}$ cycloalkyl" or "$C_{3-6}$ cycloalkyl ring" means a monocyclic saturated carbohydrate having 3-6 carbon atoms, which may be optionally substituted with one or more substituents defined in the present invention. Such examples include cyclopropyl, cyclobutyl, cyclopentyl, and cyclohexyl.

The term "$C_{3-6}$ cycloalkenyl ring" means a monocyclic carbohydrate having 3-6 carbon atoms and one or more carbon-carbon double bonds, which may be optionally substituted with one or more substituents defined in the present invention. Such examples include cyclopropene, cyclobutene, cyclopentene, and cyclohexene.

The term "3- or 6-membered heterocycloalkyl" means a 3- or 6-membered monocyclic saturated heterocycle having at least one hetero atom selected independently from the group consisting of nitrogen, oxygen, and sulfur, which may be optionally substituted with one or more substituents defined in the present invention. The nitrogen or sulfur atoms may be optionally oxidized, and the nitrogen atoms may be optionally quaternized. Such examples include azetidinyl, pyrrolidinyl, piperidinyl, piperazinyl, morpholinyl, tetrahydrofuranyl, and tetrahydropyranyl.

The term "5- or 6-membered monocyclic heterocycle" means a 5- or 6-membered monocyclic heterocycle having at least one heteroatom selected independently from the group consisting of nitrogen, oxygen, and sulfur, which may be optionally substituted with one or more substituents defined in the present invention. The ring may be saturated, partially-saturated, or unsaturated, and the nitrogen and sulfur atoms may be optionally oxidized, and the nitrogen atoms may be optionally quaternized. Such examples include pyrrolidinyl, piperidinyl, piperazinyl, morpholinyl, pyridyl, pyrrolyl, pyrazinyl, pyrimidinyl, pyridazinyl, imidazolyl, thiazolyl, pyrazolyl, oxazolyl, thienyl, and furyl.

The term "$C_{6-10}$ aryl" means a mono- or bi-cyclic aromatic hydrocarbon having 6-10 carbon atoms in which a hydrogen atom attached to the aromatic ring is excluded, and it may be optionally substituted with one or more substituents defined in the present invention. Such examples include phenyl, 1-naphthyl, 2-naphthyl, and anthracenyl.

The term "6- to 10-membered heteroaryl" means a 6- to 10-membered mono- or bi-cyclic aromatic heterocycle having at least one heteroatom selected independently from the group consisting of nitrogen, oxygen, and sulfur, and it may be optionally substituted with one or more substituents defined in the present invention. Such examples include pyridyl, pyridazinyl, isothiazolyl, pyrrolyl, furyl, thienyl, triazolyl, imidazolyl, pyrimidinyl, thiadiazolyl, pyrazolyl, oxazolyl, isoxazolyl, pyrazinyl, triazinyl, triazolyl, imidazolidinyl, oxadiazolyl, triazolyl, tetrazolyl, indolyl, indazolyl, chromenyl, quinolyl, isoquinolyl, benzofuranyl, benzothienyl, benzoxazolyl, benzothiazolyl, benzisoxazolyl, benzisothiazolyl, benzotriazolyl, and benzimidazolyl.

The term "halogen" means fluorine, chlorine, bromine, or iodine. Especially, fluorine, chlorine, or bromine is preferable.

The term "mono- or di-$C_{1-6}$ alkylamino" means an amino group in which one or two hydrogen atoms are substituted with the above alkyl groups having 1-6 carbon atoms. When hydrogen atoms are substituted with two alkyl groups, the alkyl substituents may be identical or different. Such examples include methylamino, ethylamino, dimethylamino, and diethylamino.

The term "$C_{1-4}$ acyl" means a carbonyl (—C(=O)) group to which the hydrogen atom or the above alkyl group having 1-3 carbon atoms is attached. Such examples include formyl, acetyl, and propionyl.

The term "$C_{1-6}$ haloalkyl" means the above alkyl group having 1-6 carbon atoms in which one or more hydrogen atoms are substituted with halogen atom(s). The number of substituted hydrogen atom may range from 1 to the total number of hydrogen atoms that can be present in the parent alkyl group. When multiple halogen atoms are present in the group, they may be identical or different. Such examples include chloromethyl, trifluoromethyl, and 2,2,2-trifluoroethyl.

The term "$C_{1-6}$ hydroxyalkyl" means the above alkyl having 1-6 carbon atoms in which one or more hydrogen atoms are substituted with hydroxy group(s). The number of substituted hydrogen atoms may range from one to the total number of hydrogen atoms that can be present in the parent alkyl group. Such examples include hydroxymethyl, 2-hydroxyethyl, 2-hydroxypropyl, 3-hydroxypropyl, and 4-hydroxybutyl.

The term "$C_{1-6}$ alkoxy" means a group that the above alkyl group having 1-6 carbon atoms is attachable via oxygen atom. Such examples include methoxy, ethoxy, propoxy, isopropoxy, butyloxy, pentyloxy, isopentyloxy, neopentyloxy, and hexyloxy.

The term "$C_{1-5}$ haloalkoxy" means the above alkoxy group having 1-6 carbon atoms in which one or more hydrogen atoms are substituted with halogen atom(s). The number of substituted hydrogen atoms may range from 1 to the total number of hydrogen atoms that can be present in the parent alkyl group. When multiple halogen atoms are present in the group, they may be identical or different. Such examples include chloromethoxy, trifluoromethoxy, and 2,2,2-trifluoroethoxy.

The term "$C_{1-6}$ hydroxyalkoxy" means the above alkoxy group having 1-6 carbon atoms in which one or more hydrogen atoms are substituted with hydroxy group(s). The number of substituted hydrogen atoms may range from one to the total number of hydrogen atoms that can be present in the parent alkyl group. Such examples include hydroxymethoxy, 2-hydroxyethoxy, 2-hydroxypropoxy, 3-hydroxypropoxy, and 4-hydroxybutoxy.

The term an "inhibitor of immune checkpoint" means a medicament which can inhibit activities of one or more immune checkpoint molecules (e.g. CTLA-4 and PD-1), alleviate T cell suppression, activate it, and exhibit the antitumor effect. Immune checkpoint is a protein which can inhibit the activation of killer T cells and inhibitively work on the immune system against cancer cells.

"Diseases caused by immune checkpoint" include cancers (for example, malignant melanoma, glioblastoma, lung cancer, gastric cancer, colorectal cancer, liver cancer, pancreatic cancer, renal cancer, adrenal cancer, biliary tract cancer, esophageal cancer, pharyngeal cancer, laryngeal cancer, oral cancer, bladder cancer, tongue cancer, thyroid cancer, skin cancer, breast cancer, prostate cancer, testicular cancer, uterine cancer, cervical cancer, ovarian cancer, osteosarcoma, chondrosarcoma, rhabdomyosarcoma, leiomyosarcoma, leukemia including adult T-cell leukemia, malignant lymphoma, or multiple myeloma). In the present application, the disease is preferred to be malignant melanoma.

A "pharmaceutically acceptable salt" means a salt which is formed with the compound of formula (I) of the present invention and a pharmaceutically acceptable acid or base. When the compound of formula (I) of the present invention has a basic functional group such as amino group, it may form a salt with a variety of acids. Examples of the acid addition salts include inorganic acid salts such as hydrochloride, hydrobromide, hydroiodide, sulfate, perchlorate, and phosphate, organic salts such as oxalate, malonate, maleate, fumarate, lactate, malate, citrate, tartrate, benzoate, trifluoroacetate, acetate, methanesulfonate, p-toluenesulfonate, and trifluoromethanesulfonate, and amino acid salts such as glutamate and aspartate.

When the compound of the present invention has an acidic functional group, it may form a salt with a variety of bases. Examples of the base addition salts include alkali metal salts such as sodium salts and potassium salts, alkaline earth metal salts such as calcium salts, and ammonium salts.

These salts can be obtained by ordinary methods such as recrystallization after the compound of the present invention is mixed with an acid or base.

The compound of the present invention may be present in a hydrate and/or solvate form, and the hydrate and/or solvate is also included in the compound of the present invention. The solvates include ethanol solvate and the like.

"Treatment" means the treatment and/or improvement of diseases and/or disorders in mammals, especially in humans. For example, (a) preventing diseases and/or disorders; (b) relieving and/or alleviating diseases and/or disorders, and the like are included in the present invention.

A "patient" means a human and an animal such as a dog, a cat, and a horse. Among them, a human is preferable.

A "therapeutically acceptable amount" means an amount which can provide improvement, cure, prevention and/or relief of diseases, disorders, and/or side effects, or can provide delay in the progression rate of diseases and/or disorders, compared with untreated subjects. The term includes, within its scope, an amount effective to promote normal physiological functions. On the use in the treatment, the therapeutically acceptable amount of the compound of the present invention may be construed as the administered amount of the compound ingredient. The effective dose is generally, but is not limited to, 0.001-1000 mg/kg (body weight) per day, said dose is based on the weight of the present compound.

The therapeutically effective amount includes the amount of the present compound only, or the amount of a combination of the plural present compounds, and/or the amount of the present compound in combination with other active ingredients useful for cancer treatment.

Bonds a-d, $R^1$, $R^{1'}$, $R^2$, $R^{2'}$, $R^3$-$R^8$, and Ring A of the compound represented by the formula (I) in the present invention are preferably selected as follows, but the technical scope of the present invention is not limited to the scope of the compounds listed below.

Bonds a-c: ==== denotes a single bond or a double bond, and Bond d: - - - - denotes absent or a single bond, provided that when Bond a is a double bond, Bond b is a single bond; when Bond b is a double bond, Bond a is a single bond and $R^5$ is absent; when Bond c is a double bond, $R^6$ absent; and when Bond c is a double bond and Bond d is a single bond, $R^6$ and $R^7$ are absent. Preferably, Bond a is a single bond, Bond b is a double bond, Bond c is a single or double bond, and Bond d is absent or a single bond, and more preferably, Bond a is a single bond, Bond b is a double bond, Bond c is a double bond, and Bond d is absent. When Bond d is absent, hydrogen exists at the 2nd position of the indole ring.

$R^1$, $R^{1'}$, $R^2$, and $R^{2'}$ include hydrogen, halogen, hydroxy, amino, nitro, mono- or di-$C_{1-6}$ alkyl-amino, $C_{1-5}$ alkyl, $C_{1-6}$ haloalkyl, $C_{1-6}$ hydroxyalkyl, $C_{1-6}$ alkoxy and $C_{1-6}$ haloalkoxy. Preferably, they include hydrogen, fluorine, chlorine, hydroxy, amino, methylamino, dimethylamino, methyl, trifluoromethyl, methoxy, and trifluoromethoxy, and more preferably hydrogen.

$R^3$ includes hydrogen, halogen, hydroxy, amino, nitro, mono- or di-$C_{1-6}$ alkyl-amino, $C_{1-6}$ alkyl, $C_{1-6}$ haloalkyl, $C_{1-6}$ hydroxyalkyl, $C_{1-6}$ alkoxy and $C_{1-6}$ haloalkoxy. Preferably, it includes hydrogen, $C_{1-6}$ alkyl, $C_{1-6}$ haloalkyl, $C_{1-6}$ hydroxyalkyl, $C_{1-6}$ alkoxy, and $C_{1-6}$ haloalkoxy, and more preferably, hydrogen and methyl.

$R^4$ includes hydrogen, halogen, hydroxy, amino, mono- or di-$C_{1-6}$ alkyl-amino, $C_{1-6}$ alkyl, $C_{2-6}$ alkenyl, $C_{2-6}$ alkynyl, $C_{1-6}$ alkoxy, $C_{3-6}$ cycloalkyl, 3- to 6-membered heterocycloalkyl, $C_{6-10}$ aryl, and 6- to 10-membered heteroaryl, wherein the alkyl, alkenyl, alkynyl, alkoxy, cycloalkyl, heterocycloalkyl, aryl, and heteroaryl may be independently substituted with one or more the same or different substituents selected from the group consisting of halogen, hydroxy, amino, nitro, mono- or di-$C_{1-6}$ alkylamino, $C_{1-4}$ acyl, $C_{1-6}$ alkyl, $C_{1-6}$ haloalkyl, $C_{1-6}$ hydroxyalkyl, $C_{1-6}$ alkoxy, and $C_{1-6}$ haloalkoxy, at any substitutable position. Preferably, it includes hydrogen, hydroxy, amino, mono- or di-$C_{1-6}$ alkylamino, $C_{1-6}$ alkyl, $C_{1-6}$ haloalkyl, $C_{1-6}$ hydroxyalkyl, $C_{1-6}$ alkoxy, and $C_{1-6}$ haloalkoxy, and more preferably, hydrogen, methyl, trifluoromethyl, methoxy, and trifluoromethoxy, and even more preferably, hydrogen and methoxy.

$R^5$, $R^6$, and $R^7$ include hydrogen, halogen, hydroxy, $C_{1-3}$ alkyl, $C_{1-3}$ haloalkyl, $C_{1-3}$ hydroxyalkyl, $C_{1-3}$ alkoxy, and $C_{1-3}$ haloalkoxy. Preferably, they include hydrogen, hydroxy, and $C_{1-3}$ alkyl, and more preferably, hydrogen, hydroxy, and methyl. In addition, when Bond b is a double bond, $R^5$ is absent; when Bond c is a double bond, $R^6$ is absent; when Bond c is a double bond and Bond d is a single bond, $R^7$ is absent; when Bond c is a single bond and Bond d is absent, $R^7$ is methyl; and when Bonds c and d are single bonds, $R^7$ is hydrogen.

$R^8$ includes hydrogen, halogen, hydroxy, amino, nitro, mono- or di-$C_{1-6}$ alkyl-amino, $C_{1-6}$ alkyl, $C_{2-6}$ alkenyl, $C_{2-6}$ alkynyl, $C_{1-6}$ alkoxy, benzyloxy, $C_{3-6}$ cycloalkyl, 3- to 6-membered heterocycloalkyl, $C_{6-10}$ aryl, and 6- to 10-membered heteroaryl, wherein the alkyl, alkenyl, alkynyl, alkoxy, cycloalkyl, heterocycloalkyl, aryl, or heteroaryl may be substituted with one or more the same or different groups selected from the group consisting of halogen, hydroxy, amino, nitro, mono- or di-$C_{1-6}$ alkyl-amino, $C_{1-4}$ acyl, $C_{1-6}$ alkyl, $C_{1-6}$ haloalkyl, $C_{1-6}$ hydroxyalkyl, $C_{1-6}$ alkoxy, and $C_{1-6}$ haloalkoxy, at any substitutable position. Preferably, they include hydrogen, fluorine, chlorine, bromine, hydroxy, amino, methylamino, dimethylamino, methyl, trifluoromethyl, methoxy, trifluoromethoxy, and benzyloxy, and more preferably, they include hydrogen, fluorine, chlorine, bromine, hydroxy, methyl, methoxy, and benzyloxy. In addition, when $R^8$ is hydrogen, n is 4.

Ring A includes $C_{3-6}$ cycloalkyl ring, $C_{3-6}$ cycloalkenyl ring, and 5- or 6-membered monocyclic heterocycle, wherein the cycloalkyl ring, cycloalkenyl ring, and monocyclic heterocycle may be substituted with one or more the same or different groups selected from the group consisting of halogen, hydroxy, oxo, amino, nitro, mono- or di-$C_{1-6}$ alkyl-amino, $C_{1-4}$ acyl, $C_{1-6}$ alkyl, $C_{1-6}$ haloalkyl, $C_{1-6}$ hydroxyalkyl, $C_{1-6}$ alkoxy, and $C_{1-6}$ haloalkoxy, at any substitutable position. Preferably, it includes $C_{5-6}$ cycloalkyl ring, $C_{5-6}$ cycloalkenyl ring, and 5- or 6-membered saturated monocyclic heterocycle, wherein the cycloalkyl ring, cycloalkenyl ring, and saturated monocyclic heterocycle may be substituted with one or more the same or different groups selected from the group consisting of hydroxy, oxo, $C_{1-6}$ alkyl, $C_{1-6}$ haloalkyl, $C_{1-6}$ hydroxyalkyl, $C_{1-6}$ alkoxy, and $C_{1-6}$ haloalkoxy, at any substitutable position. More preferably, it includes the following groups:

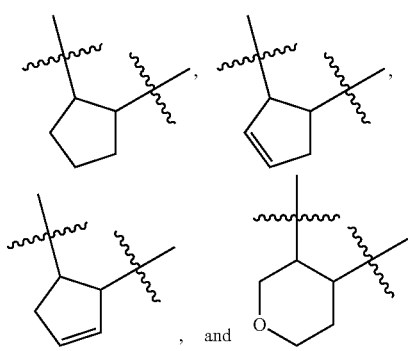

which may be substituted with one or more the same or different groups selected from the group consisting of hydroxy, oxo, $C_{1-3}$ alkyl, $C_{1-3}$ hydroxyalkyl, and $C_{1-3}$ alkoxy. Even more preferably, it includes the following groups:

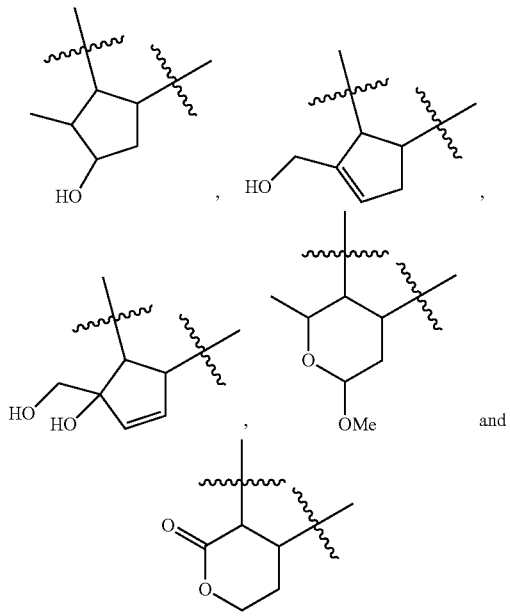

The compound of the present invention may have one or more asymmetric carbon atoms, geometrical isomerisms, or axial chirality, and therefore, it may be presented in several kinds of optical isomers or stereoisomers. Such stereoisomers, and mixture and racemates thereof are included in the present invention.

In addition, the present invention also encompasses a deuterated compound in which one or more $^1H$ in the present compound is substituted with $^2H$ (D).

The compound of the present invention or pharmaceutically acceptable salt which is obtained as a crystal may have crystalline polymorphisms, and such polymorphisms are also included in the present invention.

Methods for preparing the compound of the present invention are illustrated below using examples, but the present invention is not limited to them. As shown below, the representative compounds of formula (I) of the present invention can be prepared from plant extracts which are chemically modified (diversity-enhanced extracts) (Org. Lett. 2014, 16, 1916-1919). In addition, compounds 8-17 can be prepared by replacing tryptamine in step 3 with a substituted tryptamine such as 6-methoxytryptamine.

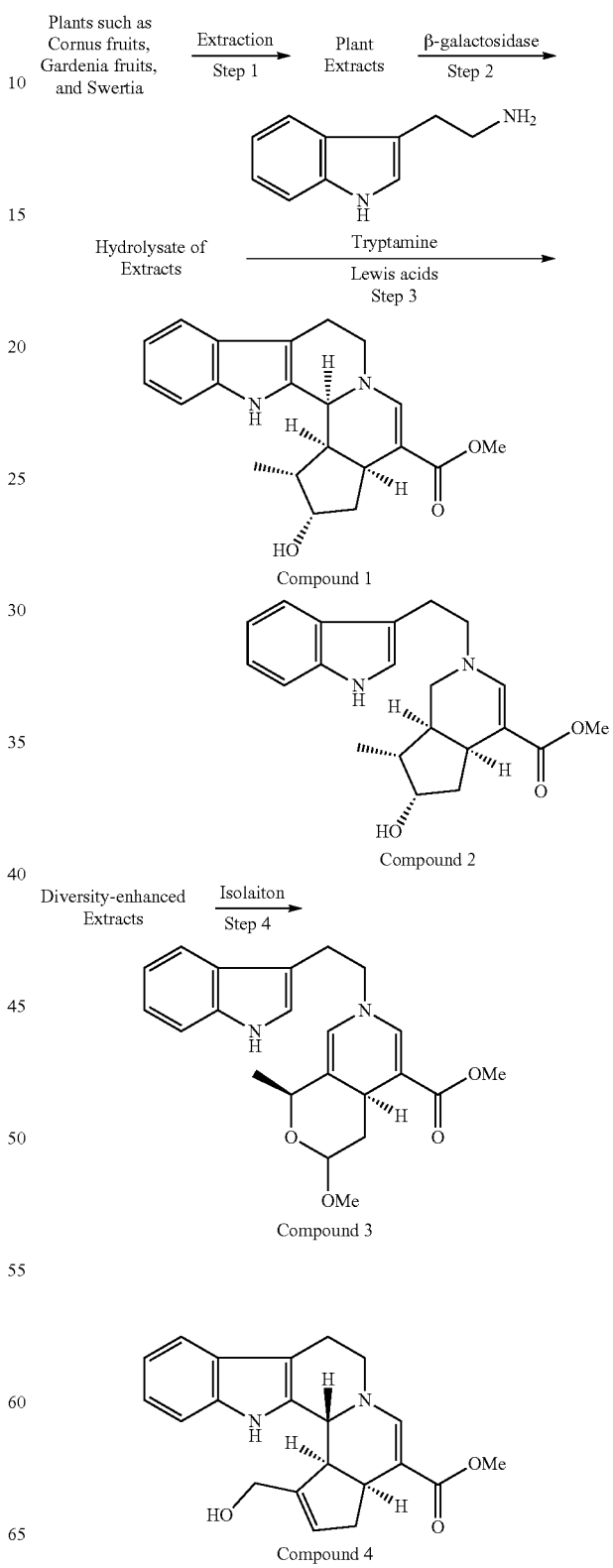

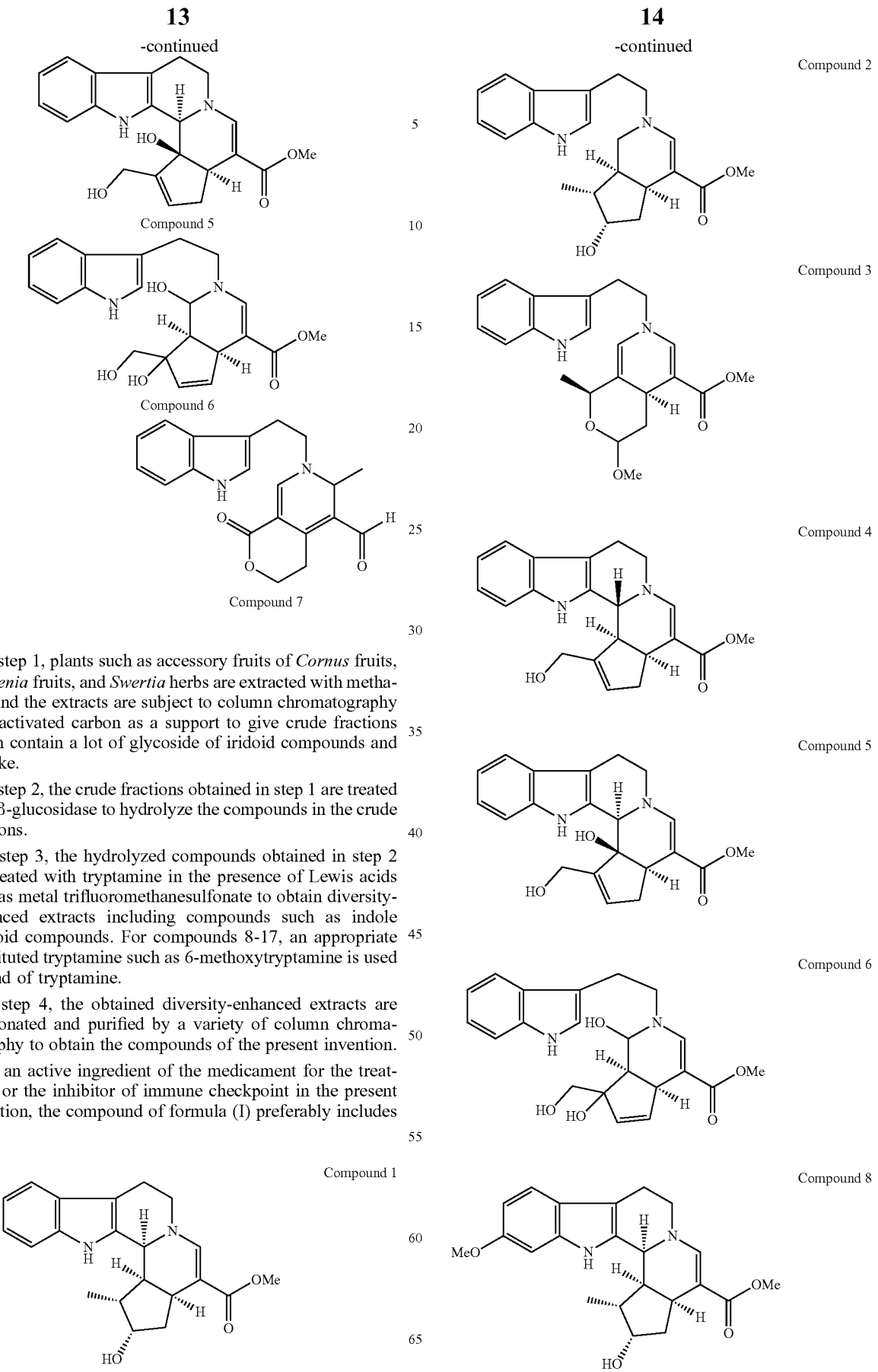

In step 1, plants such as accessory fruits of *Cornus* fruits, *Gardenia* fruits, and *Swertia* herbs are extracted with methanol, and the extracts are subject to column chromatography with activated carbon as a support to give crude fractions which contain a lot of glycoside of iridoid compounds and the like.

In step 2, the crude fractions obtained in step 1 are treated with β-glucosidase to hydrolyze the compounds in the crude fractions.

In step 3, the hydrolyzed compounds obtained in step 2 are treated with tryptamine in the presence of Lewis acids such as metal trifluoromethanesulfonate to obtain diversity-enhanced extracts including compounds such as indole alkaloid compounds. For compounds 8-17, an appropriate substituted tryptamine such as 6-methoxytryptamine is used instead of tryptamine.

In step 4, the obtained diversity-enhanced extracts are fractionated and purified by a variety of column chromatography to obtain the compounds of the present invention.

As an active ingredient of the medicament for the treatment or the inhibitor of immune checkpoint in the present invention, the compound of formula (I) preferably includes -continued
Compound 9
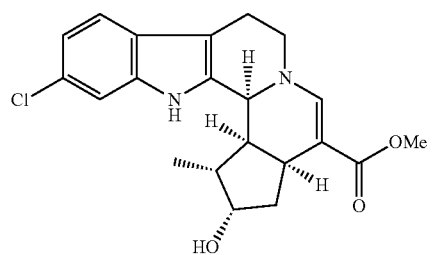
Compound 10
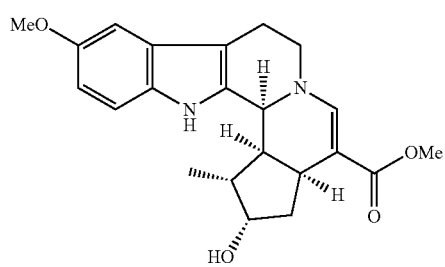
Compound 11
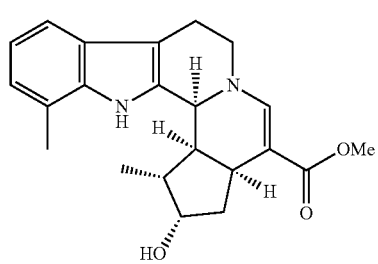
Compound 12
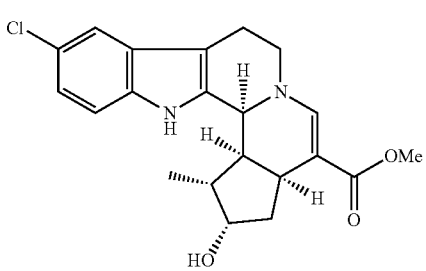
Compound 13
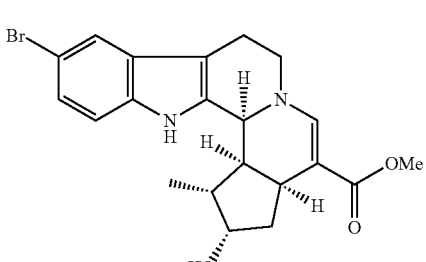
Compound 14
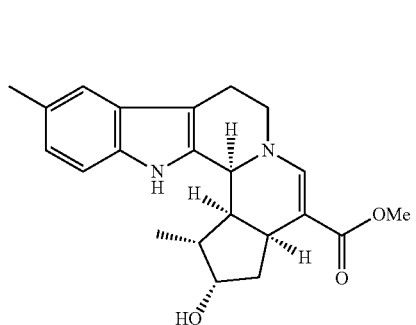
-continued
Compound 15
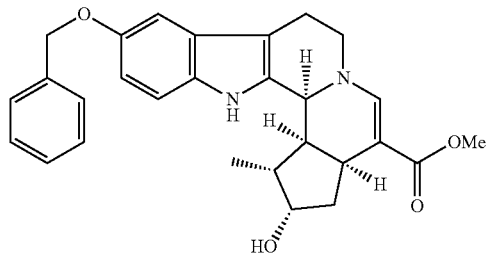
Compound 16
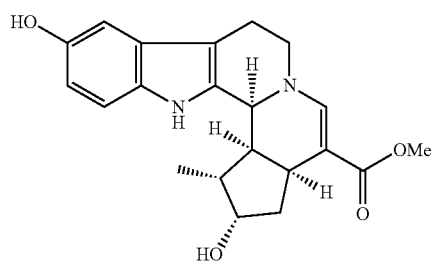
Compound 17
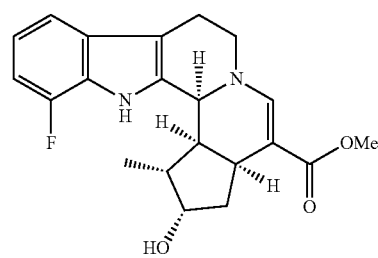
and more preferably, it includes
Compound 1
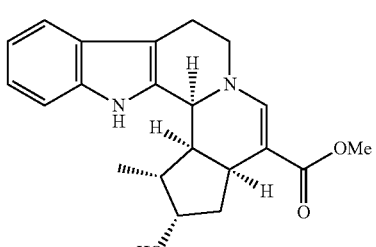
Compound 2
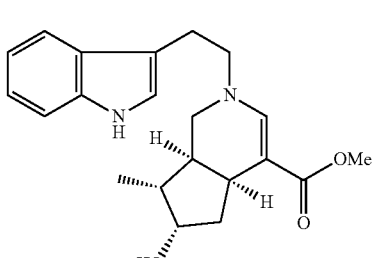
Compound 4
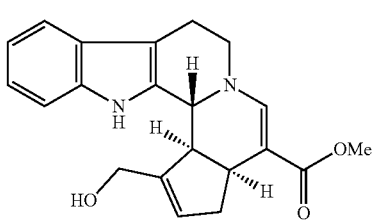

-continued
Compound 8
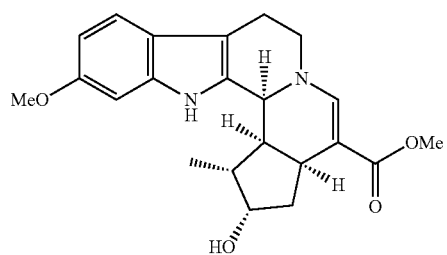
Compound 9
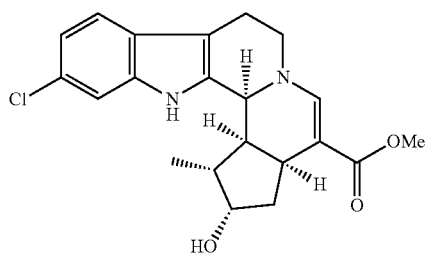
Compound 10
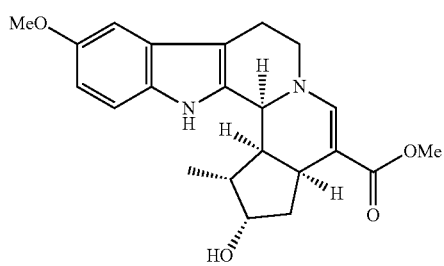
Compound 11
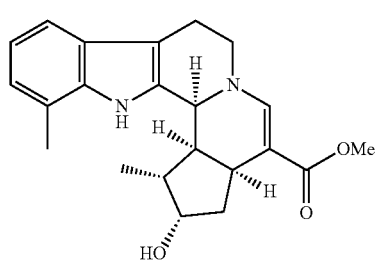
Compound 12
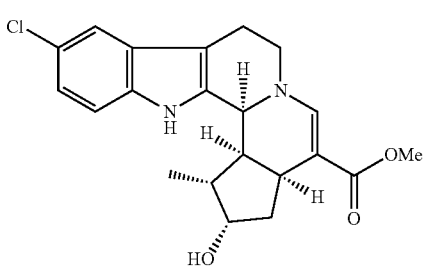
Compound 13
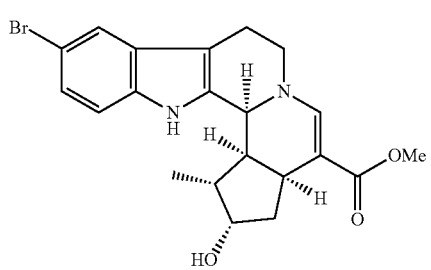
-continued
Compound 14
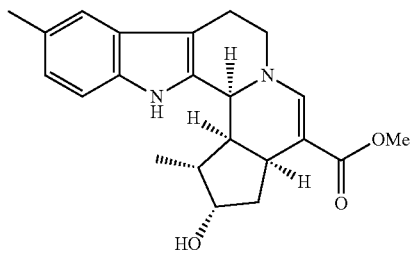
Compound 15
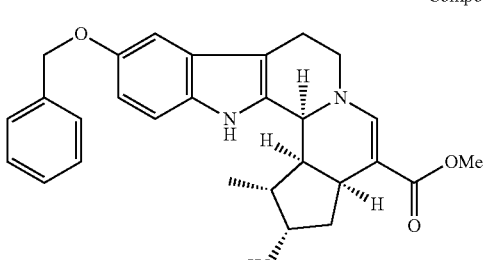
Compound 16
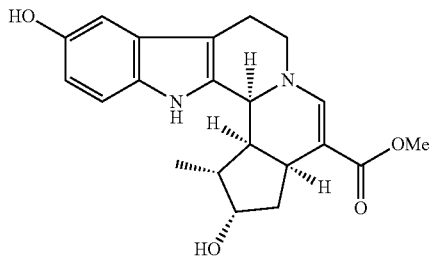
Compound 17
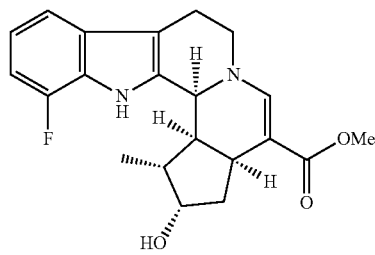
and even more preferably, it includes
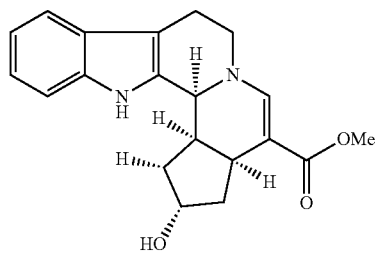
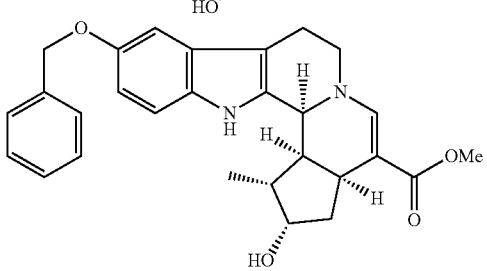

-continued

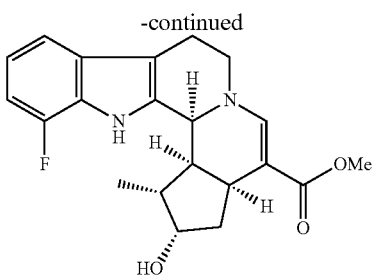

The medicament for the treatment or inhibitor of immune checkpoint in the present invention comprises the compound of the present invention as an active ingredient, and may further comprise other ingredients as long as they do not prevent the inhibitory effect on immune checkpoint. The proportion of the present compound in the medicament or inhibitor of immune checkpoint of the present invention is not limited to specific ones. For example, the medicament of the present invention may comprise 0.1% by weight or more, or 0.5% by weight or more, or 1.0% by weight or more of the present compound, and 0.1-70% by weight is preferable. Alternatively, the medicament for the treatment or inhibitor of immune checkpoint of the present invention may consist of only the compound of the present invention.

The compound of the present invention can be orally or parenterally (e.g., intravenously, topically, transnasally, pulmonarily, and rectally) administered. The dosage form of the present invention can be optionally selected and prepared according to physical and health condition, etc. of a subject. For example, the compound of the present invention can be prepared as a dosage form for oral administration such as a tablet, a capsule, a granule, a powder, a solution, and a syrup, or a dosage form for parenteral administration such as an injection, a dialysis agent, an inhalant, a suppository, eye drops, an ophthalmic ointment, ear drops, nasal drops, a topical agent, a spray, an ointment, a cream, a gel, and a patch, by ordinary methods.

The medicament for the treatment or the inhibitor of immune checkpoint of the present invention may comprise if necessary, one or more kinds of pharmaceutically acceptable carriers such as an excipient (including lactose, white soft sugar, D-mannitol, and crystalline cellulose), a disintegrant (including carmellose, carmellose sodium, and low substituted hydroxypropyl cellulose), a bonding agent (including hydroxypropyl cellulose, hydroxypropylmethyl cellulose, povidone, and crystalline cellulose), a lubricant (including magnesium stearate, calcium stearate, and talc), a solvent (including water, ethanol, and propylene glycol), a buffering agent (including tribasic sodium phosphate, sodium hydrogen phosphate, and sodium dihydrogen phosphate), a suspending agent (including gum arabic, tragacanth, and carboxymethyl cellulose sodium), an emulsifier (including glycerol fatty acid ester and sorbitan fatty acid ester) and the like.

The dosage of the compound of the present invention may be selected according to a mode of administration, an age of a subject, a degree of a disease, a symptom, a dosage form and the like, and as an example, the compound may be orally administered at a dose of 0.01 mg-0.1 mg, 0.1 mg-1 mg, 1 mg-5 mg, 5 mg-10 mg, 10 mg-50 mg, 50 mg-100 mg, 100 mg-500 mg, 500 mg-1 g, 1 g-1.5 g, 1.5 g-2 g, 2 g-5 g, or 5 g-10 g per day. The daily dosage of the compound of the present invention may be administered in one or several portions.

EXAMPLES

The present invention is exemplified in more detail in the following examples and tests, however, these are not meant to limit the present invention. The compounds are identified by NMR spectroscopy, mass spectrometry and the like.

The following abbreviations may be used in the examples to simplify the description of the specification. Abbreviations used for NMR are defined as follows: s for singlet, d for doublet, dd for doublet of doublets, ddd for doublet of doublet of doublets, dt for doublet of triplets, t for triplet, td for triplet of doublets, q for quartet, m for multiplet, br for broadened, brs for broad singlet, and J for coupling constants.

Example 1: Preparation of Compound 1-3

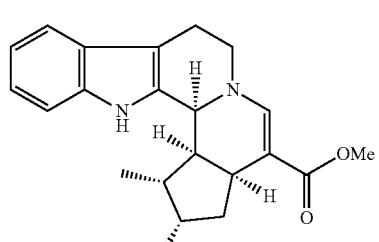

Compound 1

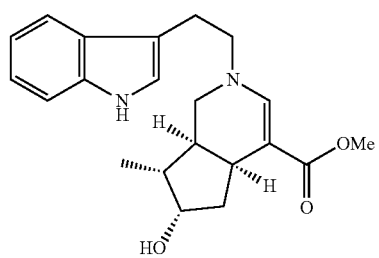

Compound 2

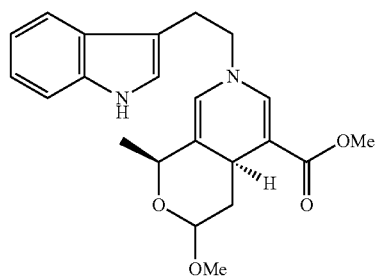

Compound 3

Step 1:

To accessory fruits of *Cornus* fruits (42 g) (purchased from Kinokuniya Kan Pharmacy Co., Ltd.) was added methanol (0.5 L) and the mixture was left for 2 days for extraction. The resulting extraction was concentrated under reduced pressure to give methanol extract (21 g). The methanol extract was suspended in ethyl acetate (50 mL), extracted three times with water (50 mL) to give a water-soluble portion. The water soluble portion was added into activated carbon (15 g), and eluted successively with water (0.2 L), 5% ethanol solution (0.2 L) and methanol (0.2 L) and the methanol eluent was concentrated under reduced pressure to give a crude fraction (1.55 g) which contains a lot of glycoside of iridoid compounds and the like.

Step 2:

The resulting crude fraction was suspended in 0.05 M citrate buffer (pH 6.0) (50 mL) and β-glucosidase (derived from sweet almonds, Toyobo) (36 mg) was added thereto and the mixture was stirred at 45° C. for two days. The reaction solution was extracted three times with ethyl acetate (50 mL), and the combined ethyl acetate extract was washed with water (100 mL), dried with anhydrous sodium sulfate, and then the solvent was removed under reduced pressure to give a hydrolysate (203 mg).

Step 3:

The resulting hydrolysate was dissolved in dichloromethane (13.5 mL), and tryptamine (131 mg, 0.82 mmol) and bismuth(III) trifluoromethanesulfonate (54 mg, 0.082 mmol) were added thereto, and stirred at room temperature for 24 hours. To the reaction solution was added aqueous saturated sodium bicarbonate solution (30 mL) and the mixture was extracted three times with ethyl acetate (50 mL). The extracted ethyl acetate layer was combined, washed with brine (100 mL), dried with anhydrous sodium sulfate, and then concentrated under reduced pressure to obtain diversity-enhanced extract (197 mg) comprising compounds such as indole alkaloid compounds.

Step 4:

The resulting diversity-enhanced extract was subjected to silica gel column chromatography to obtain fraction A (10.4 mg) eluted with hexane-ethyl acetate (4:1), fraction B (16.7 mg) eluted with hexane-ethyl acetate (2:1), fraction C (30.5 mg) elated with hexane-ethyl acetate (1:1), fraction D (30.9 mg) elated with hexane-ethyl acetate (1:2), and fraction E (57.5 mg) eluted with ethyl acetate.

Step 5:

The fraction B was subjected again to silica gel column chromatography to get compound 1 (2.5 mg) from fraction elated with hexane-ethyl acetate (2:1). The fraction D was subjected again to silica gel column chromatography to get compound 2 (8.4 mg) from fraction elated with hexane-ethyl acetate (1:1). In addition, the fraction D was eluted with hexane-ethyl acetate (1:2) to get fraction D-1 (7.8 mg) and the resulting fraction was further subjected to silica gel column chromatography to get compound 3 (2.5 mg) from fraction elated with chloroform-methanol (99:1).

Compounds 1-3 were analyzed by mass spectrometry based on EIMS (electron impact mass spectrometry), and NMR. The results of EIMS and NMR are shown below.

Compound 1:

$^1$H-NMR (600 MHz, CDCl$_3$) δ 8.05 (1H, br.s), 7.56 (1H, dd, J=7.9, 1.0 Hz), 7.36 (1H, dd, J=8.2, 1.0 Hz), 7.35 (1H, s), 7.19 (1H, ddd, J=8.2, 7.6, 1.0 Hz), 7.12 (1H, ddd, J=8.2, 7.6, 1.0 Hz), 6.96 (1H, d, J=2.5 Hz), 4.09-4.12 (1H, m), 3.63 (3H, s), 3.42 (2H, t, J=7.4 Hz), 3.12 (1H, dd, J=12.2, 4.7 Hz), 3.04 (1H, td, J=8.2, 7.4 Hz), 2.98 (2H, dt, J=7.4, 2.5 Hz), 2.75 (1H, dd, J=12.2, 6.7 Hz), 2.20 (1H, ddd, J=14.2, 7.4, 1.5 Hz), 1.87-1.92 (1H, m), 1.66-1.70 (1H, m), 1.56 (1H, ddd, J=14.2, 8.1, 5.6 Hz), 1.00 (3H, d, J=7.0 Hz).

$^{13}$C-NMR (150 MHz, CDCl$_3$) δ 169.3, 145.9, 136.3, 127.1, 122.2, 122.0, 119.5, 118.5, 112.5, 111.3, 99.9, 74.5, 56.2, 50.5, 47.3, 43.1, 42.0, 41.6, 32.4, 25.1, 13.0.

EIMS m/z (rel. int) 354 [M]$^+$ (40), 224 (100), 192 (36).

HREIMS m/z 354.1934 (Calculated mass of $C_{21}H_{26}O_3N_2$ 354.1943).

Compound 2:

$^1$H-NMR (600 MHz, CDCl$_3$) δ 8.31 (1H, br.s), 7.45 (1H, d, J=7.6 Hz), 7.36 (1H, s), 7.32 (1H, d, J=7.6 Hz), 7.15 (1H, t, J=7.6 Hz), 7.10 (1H, t, J=7.6 Hz), 4.39 (1H, brs), 4.24 (1H, t, J=5.4 Hz), 3.73 (1H, dd, J=15.8, 5.4 Hz), 3.62 (3H, s), 3.46 (1H, J=15.8, 5.8 Hz), 2.98 (1H, ddd, J=9.8, 8.0, 6.7 Hz), 2.90-2.95 (1H, m), 2.77 (1H, dd, J=15.1, 5.4 Hz), 2.41 (1H, ddd, J=10.1, 9.8, 2.5 Hz), 2.24 (1H, dd, J=14.7, 8.0 Hz), 2.05-2.11 (1H, m), 1.80 (1H, ddd, J=14.7, 6.7, 5.3), 1.20 (3H, d, J=6.9 Hz).

$^{13}$C-NMR (150 MHz, CDCl$_3$) δ 168.6, 144.7, 135.8, 133.4, 127.1, 121.9, 119.6, 118.0, 111.0, 108.6, 104.3, 74.5, 52.8, 51.5, 50.6, 44.9, 42.5, 41.5, 30.9, 22.2, 12.8.

EIMS m/z (rel. int) 352 [M]$^+$ (100), 293 (57), 279 (32), 255 (22), 224 (12), 170 (17).

HREIMS m/z 352.1806 (Calculated mass of $C_{21}H_{24}O_3N_2$ 352.1787).

Compound 3:

$^1$H-NMR (600 MHz, CDCl$_3$) δ 8.08 (1H, br.s), 7.55 (1H, dd, J=8.0, 1.0 Hz), 7.35 (1H, dd, J=8.0, 0.9 Hz), 7.19 (1H, td, J=8.0, 1.0 Hz), 7.13 (1H, td, J=8.0, 0.9 Hz), 7.00 (1H, d, J=2.6 Hz), 6.93 (1H, d, J=2.6 Hz), 5.42 (1H, br.s), 4.75 (1H, d, J=2.8 Hz), 4.21 (1H, q, J=6.5 Hz), 3.92 (1H, dd, J=12.1, 3.9 Hz), 3.62 (3H, s), 3.38 (2H, t, J=7.1 Hz), 3.35 (3H, s), 2.98 (2H, t, J=7.1 Hz), 2.23 (1H, dd, J=12.7, 3.9 Hz), 1.78 (1H, ddd, J=12.7, 12.1, 2.8 Hz), 1.05 (3H, d, J=6.5 Hz).

$^{13}$C-NMR (150 MHz, CDCl$_3$) δ 168.5, 141.3, 136.3, 127.0, 122.5, 122.2, 121.1, 120.2, 119.6, 118.4, 111.9, 111.3, 99.8, 99.5, 64.6, 54.6, 54.4, 50.7, 39.0, 29.3, 26.2, 16.5.

EIMS m/z (rel. int) 382 [M]$^+$ (23), 351 (13), 323 (32), 144 (100).

HREIMS m/z 382.0962 (Calculated mass of $C_{22}H_{26}O_4N_2$ 382.1893).

Example 2: Preparation of Compound 4-6

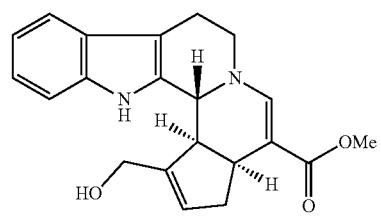

Compound 4

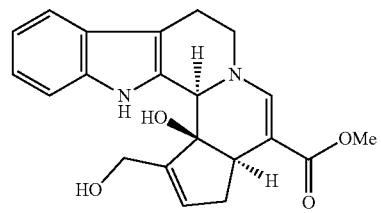

Compound 5

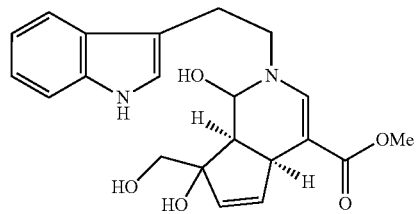

Compound 6

To *Gardenia* fruits (30 g) (purchased from Kinokuniya Kan Pharmacy Co., Ltd.) was added methanol (0.5 L) and then the mixture was left for 2 days for extraction. The resulting extract was concentrated under reduced pressure to give methanol extract (7.5 g). From the resulting methanol extract, diversity-enhanced extract (478 mg) comprising compounds such as indole alkaloid compounds was obtained according to the same procedures as steps 1-3 of Example 1.

The resulting diversity-enhanced extract was subjected to silica gel column chromatography to obtain fraction A (4.3 mg) eluted with hexane-ethyl acetate (3:1), fraction B (17.5 mg) eluted with hexane-ethyl acetate (1:1), fraction C (34.0 mg) eluted with hexane-ethyl acetate (1:3), fraction D (74.3 mg) eluted with hexane-ethyl acetate (1:9), and fraction E (285.2 mg) eluted with ethyl acetate.

The fraction B was subjected to column chromatography with octadecyl-silylated silica gel as a support to give compound 4 (2.2 mg) from a fraction eluted with water-acetonitrile (3:2). In addition, the fraction D was subjected to column chromatography with octadecyl-silylated silica gel as a support to give compound 5 (3.0 mg) from a fraction eluted with water-acetonitrile (1:1) and compound 6 (4.4 mg) from a fraction eluted with water-acetonitrile (2:3), respectively.

Compounds 4-6 were analyzed by mass spectrometry based on EIMS (electron impact mass spectrometry), and NMR. The results of EIMS and NMR are shown below.

Compound 4:

$^1$H-NMR (600 MHz, CDCl$_3$) δ 9.99 (1H, br.s), 7.55 (1H, s), 7.45 (1H, d, J=7.7 Hz), 7.33 (1H, d, J=8.0 Hz), 7.14 (1H, t, J=8.0 Hz), 7.08 (1H, dd, J=8.0, 7.7 Hz), 6.01 (1H, br.s), 4.44 (1H, d, J=13.0 Hz), 4.34 (1H, d, J=7.6 Hz), 4.32 (1H, d, J=13.0 Hz), 3.72 (1H, dd, J=15.6, 4.2 Hz), 3.67 (3H, s), 3.56 (1H, td, J=12.3, 4.1 Hz), 3.25 (1H, q, J=8.0 Hz), 2.91-2.95 (1H, m), 2.88-2.91 (1H, m), 2.87 (1H, dd, J=8.0, 7.6 Hz), 2.75-2.78 (1H, m), 2.56 (1H, br.s), 2.10 (1H, ddd, J=16.7, 8.0, 2.1 Hz).

$^{13}$C-NMR (150 MHz, CDCl$_3$) δ 168.9, 145.3, 144.4, 136.2, 133.4, 133.1, 126.6, 121.8, 119.4, 117.9, 111.3, 108.8, 99.0, 60.9, 54.1, 52.1, 50.6, 47.0, 39.6, 36.8, 22.1.

EIMS m/z (rel. int) 350 [M]$^+$ (100), 319 (26), 291 (26), 279 (50), 170 (39).

HREIMS m/z 350.1619 (Calculated mass of C$_{21}$H$_{22}$O$_3$N$_2$ 350.1630).

Compound 5:

$^1$H-NMR (600 MHz, CDCl$_3$) δ 9.58 (1H, br.s), 7.49 (1H, s), 7.46 (1H, d, J=8.0 Hz), 7.31 (1H, d, J=8.0 Hz), 7.15 (1H, t, J=8.0 Hz), 7.08 (1H, t, J=8.0 Hz), 6.15 (1H, br.s), 4.65 (1H, br.s), 4.37 (1H, d, J=12.2 Hz), 4.23 (1H, d, J=12.2 Hz), 3.72 (1H, dd, J=12.6, 4.7 Hz), 3.63 (3H, s), 3.48 (1H, td, J=12.6, 4.4 Hz), 2.93-2.99 (3H, m), 2.82 (1H, dd, J=15.3, 4.4 Hz), 2.15-2.18 (1H, m).

$^{13}$C-NMR (150 MHz, CDCl$_3$) δ 168.2, 145.9, 144.8, 135.9, 135.7, 130.1, 126.5, 122.0, 119.4, 117.9, 111.2, 110.2, 103.6, 83.3, 58.5, 56.5, 51.4, 50.8, 45.1, 37.7, 21.9.

EIMS m/z (rel. int) 366 [M]$^+$ (100), 335 (21), 305 (20), 255 (86), 169 (36), 144 (44).

HREIMS m/z 366.1586 (Calculated mass of C$_{21}$H$_{22}$O$_4$N$_2$ 366.1580).

Compound 6:

$^1$H-NMR (600 MHz, CDCl$_3$) δ 8.04 (1H, br.s), 7.56 (1H, dd, J=8.1, 0.9 Hz), 7.35 (1H, dd, J=8.1, 0.8 Hz), 7.30 (1H, s), 7.19 (1H, td, J=8.1, 0.9 Hz), 7.11 (1H, td, J=8.1, 0.8 Hz), 6.97 (1H, J=2.2 Hz), 6.10 (1H, dd, J=5.4, 2.1 Hz), 5.61 (1H, dd, J=5.4, 2.7 Hz), 4.90 (1H, d, J=6.9 Hz), 3.82 (1H, d, J=9.4 Hz), 3.81-3.83 (1H, m), 3.67 (3H, s), 3.60-3.65 (1H, m), 3.59 (1H, d, J=9.4 Hz), 3.50-3.56 (1H, m), 3.02-3.11 (2H, m), 2.43 (1H, dd, J=9.1, 6.9 Hz).

$^{13}$C-NMR (150 MHz, CDCl$_3$) δ 168.5, 142.2, 139.3, 136.3, 131.1, 127.2, 122.2, 122.1, 119.5, 118.6, 112.5, 111.2, 97.4, 94.5, 87.4, 72.3, 54.7, 50.8, 47.4, 39.3, 25.9.

EIMS m/z (rel. int) 366 [M-H$_2$O]$^+$ (50), 236 (100), 206 (240).

HREIMS m/z 366.1596 (Calculated mass of C$_{21}$H$_{24}$O$_5$N$_2$ 366.1580).

Example 3: Preparation of Compound 7

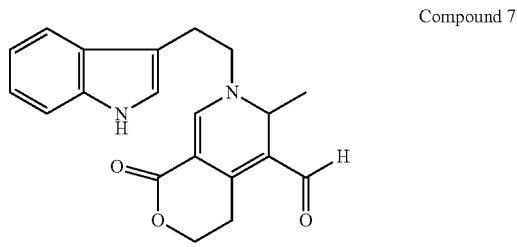 [SMILES: CC1C(C=O)=C2CCOC(=O)C2=CN1CCc1c[nH]c2ccccc12]

Compound 7

To *Swertia* herbs (73 g) (purchased from Kinokuniya Kan Pharmacy Co., Ltd.) was added methanol (0.8 L), and then the mixture was left for two days for extraction. The resulting extract was concentrated under reduced pressure to give methanol extract (21.6 g). From the resulting methanol extract, diversity-enhanced extract (737 mg) comprising compounds such as indole alkaloid compounds was obtained according to the same procedures as steps 1-3 of Example 1.

The resulting diversity-enhanced extract was subject to silica gel column chromatography to obtain fraction A (243.1 mg) eluted with chloroform-methanol (99:1), fraction B (59.5 mg) eluted with chloroform-methanol (197:3), fraction C (91.7 mg) eluted with chloroform-methanol (49:1), fraction D (59.8 mg) eluted with chloroform-methanol (19:1), and fraction E (196.2 mg) eluted with methanol, respectively.

The resulting fraction B was subjected to column chromatography with octadecyl-silylated silica gel as a support to give compound 7 (3.5 mg) from a fraction eluted with water-acetonitrile (3:2).

Compound 7 was analyzed by mass spectrometry based on EIMS (electron impact mass spectrometry), and NMR.

$^1$H-NMR (600 MHz, CDCl$_3$) δ 9.61 (1H, s), 8.10 (1H, br.s), 7.55 (1H, s), 7.45 (1H, dd, J=7.9, 0.9 Hz), 7.34 (1H, dd, J=8.2, 0.8 Hz), 7.18 (1H, ddd, J=8.2, 8.0, 0.9 Hz), 7.07 (1H, td, J=8.0, 0.8 Hz), 6.96 (1H, d, J=2.0 Hz), 4.79 (1H, q, J=6.4 Hz), 4.20-4.28 (2H, m), 3.75-3.82 (1H, m), 3.56-3.63 (1H, m), 3.10-3.16 (2H, m), 2.94 (1H, dt, J=16.4, 4.6 Hz), 2.85 (1H, ddd, J=16.4, 8.8, 5.4 Hz), 1.13 (3H, d, J=6.4 Hz).

$^{13}$C-NMR (150 MHz, CDCl$_3$) δ 184.4, 165.2, 151.9, 147.7, 136.2, 126.9, 122.5, 122.2, 119.7, 118.1, 115.1, 111.4, 110.9, 95.2, 64.8, 56.2, 51.3, 25.0, 23.1, 18.5.

EIMS m/z (rel. int) 336 [M]$^+$ (18), 321 (26), 144 (100), 130 (39).

HREIMS m/z 336.1454 (Calculated mass of C$_{20}$H$_{20}$O$_3$N$_2$ 336.1474).

Example 4: Preparation of Compound 8

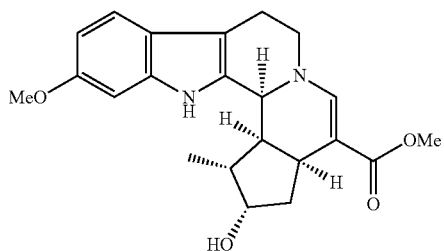

Compound 8

Diversity-enhanced extract (213 mg) comprising indole alkaloid compounds was obtained according to the same procedure as steps 1-3 of Example 1 with the exception that 6-methoxytryptamine (126 mg, 0.66 mmol) was used instead of tryptamine in step 3. The resulting diversity-enhanced extracts were subjected to silica gel column chromatography to give fraction A (102 mg) eluted with chloroform-methanol (49:1). The fraction A was subjected to recycle high performance liquid chromatography (Column: YMC-GPC T-2000, Elution solvent: ethyl acetate, Flow rate: 8 mL/min), and fraction eluted in 12-13 min was repeatedly resolved 5 times in the same column to give compound 8 (65 mg).

Compound 8 was analyzed by mass spectrometry based on EIMS (electron impact mass spectrometry), and NMR. The results of EIMS and NMR are shown below.

$^1$H-NMR (600 MHz, CDCl$_3$) δ 8.61 (1H, br.s), 7.34 (1H, s), 7.29 (1H, d, J=8.5 Hz), 6.81 (1H, d, J=2.2 Hz), 6.75 (1H, dd, J=8.5, 2.2 Hz), 4.32 (1H, br.s), 4.20 (1H, t, J=4.8 Hz), 3.79 (3H, s), 3.66 (1H, dd, J=13.1, 5.9 Hz), 3.60 (3H, s), 3.40 (1H, ddd, J=13.1, 12.0, 4.4 Hz), 2.91-2.97 (1H, m), 2.83-2.90 (1H, m), 2.68 (1H, dd, J=15.2, 4.4 Hz), 2.39 (1H, ddd, J=9.7, 8.2, 4.0 Hz), 2.23 (1H, ddd, J=14.7, 7.9, 0.9 Hz), 1.99-2.05 (1H, m), 1.77 (1H, dt, J=14.7, 5.9 Hz), 1.15 (3H, d, J=7.0 Hz).

$^{13}$C-NMR (150 MHz, CDCl$_3$) δ 168.8, 156.2, 144.9, 136.6, 132.2, 121.5, 118.4, 109.0, 108.1, 104.0, 95.2, 74.3, 55.7, 52.8, 51.5, 50.6, 44.7, 42.3, 41.4, 30.8, 22.2, 12.8.

EIMS m/z (rel. int) 382 [M]$^+$ (100), 365 (24), 323 (77), 311 (30), 200 (22).

HREIMS m/z 382.1851 (Calculated mass of C$_{22}$H$_{26}$O$_4$N$_2$ 382.1893).

Example 5: Preparation of Compound 9

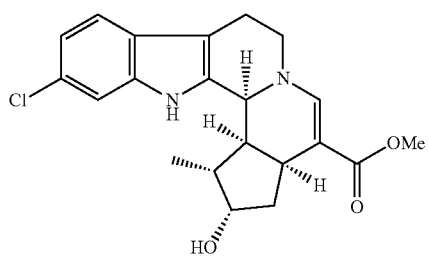

Compound 9

Compound 9 (4.3 mg) was obtained according to the same method as Example 4 with the exception that 6-chlorotryptamine (110 mg, 0.57 mmol) was used instead of 6-methoxytryptamine (126 mg, 0.66 mmol) in step 3.

Compound 9 was analyzed by mass spectrometry based on EIMS (electron impact mass spectrometry), and NMR. The results of EIMS and NMR are shown below.

$^1$H-NMR (600 MHz, CDCl$_3$) δ 8.20 (1H, br.s), 7.32 (1H, d, J 1.3 Hz), 7.30 (1H, d, J=8.4 Hz), 7.28 (1H, d, J=1.8 Hz), 7.04 (1H, dd, J=8.4, 1.8 Hz), 4.35 (1H, br.s), 4.22 (1H, t, J=4.6 Hz), 3.71 (1H, dd, J=13.3, 5.5 Hz), 3.61 (3H, s), 3.43 (1H, ddd, J=13.3, 11.8, 4.8 Hz), 2.92-2.97 (1H, m), 2.85-2.91 (1H, m), 2.70 (1H, dd, J=15.3, 4.8 Hz), 2.38 (1H, ddd, J=9.8, 8.2, 4.0 Hz), 2.22 (1H, ddd, 14.8, 7.8, 1.1 Hz), 2.02-2.08 (1H, m), 1.79 (1H, dt, J=14.8, 5.7 Hz), 1.17 (3H, d, J=7.1 Hz).

$^{13}$C-NMR (150 MHz, CDCl$_3$) δ 168.5, 144.4, 136.1, 134.1, 127.7, 125.8, 120.4, 118.8, 111.0, 108.8, 104.8, 74.5, 52.7, 51.3, 50.7, 44.8, 42.5, 41.4, 30.9, 22.0, 12.7.

EIMS m/z (rel. int) 388 [M+2]$^+$ (33), 386 [M]$^+$ (100), 327 (72), 313 (48), 289 (39), 204 (30).

HREIMS m/z 386.1431 (Calculated mass of C$_{21}$H$_{23}$O$_3$N$_2$$^{35}$Cl 386.1397).

Example 6: Preparation of Compound 10

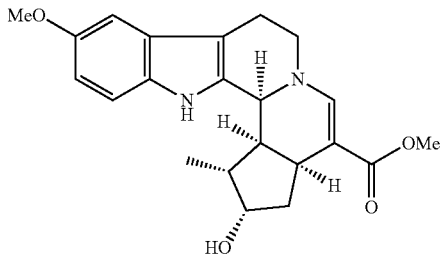

Compound 10

Compound 10 (9.5 mg) was obtained according to the same method as Example 4 with the exception that 5-methoxytryptamine (26 mg, 0.14 mmol) was used instead of 6-methoxytryptamine (126 mg, 0.66 mmol) in step 3.

Compound 10 was analyzed by mass spectrometry based on EIMS (electron impact mass spectrometry), and NMR. The results of EIMS and NMR are shown below.

$^1$H-NMR (600 MHz, CDCl$_3$) δ 8.20 (1H, br.s), 7.33 (1H, s), 7.19 (1H, d, J=8.8 Hz), 6.87 (1H, d, J=2.4 Hz), 6.79 (1H, dd, J=8.8, 2.4 Hz), 4.35 (1H, br.s), 4.20 (15, t, J=5.5 Hz), 3.82 (3H, s), 3.70 (1H, dd, J=13.1, 5.7 Hz), 3.59 (3H, s), 3.43 (1H, ddd, J=13.1, 12.0, 4.7 Hz), 2.91-2.96 (1H, m), 2.85-2.91 (1H, m), 2.70 (1H, dd, J=15.1, 4.7 Hz), 2.36 (1H, ddd, J=9.7, 8.1, 3.8 Hz), 2.18 (1H, ddd, J=14.7, 8.1, 1.2 Hz), 2.00-2.07 (1H, m), 1.77 (15, dt, J=14.7, 5.9 Hz), 1.16 (3H, d, J=7.0 Hz).

$^{13}$C-NMR (150 MHz, CDCl$_3$) δ 168.6, 154.2, 144.6, 134.2, 130.9, 127.5, 111.74, 111.73, 108.4, 104.4, 100.2, 74.5, 56.0, 52.9, 51.5, 50.6, 44.8, 42.5, 41.4, 30.9, 22.2, 12.8.

EIMS m/z (rel. int) 382 [M]$^+$ (100), 364 (90), 323 (66), 200 (52), 129 (81).

HREIMS m/z 382.1896 (Calculated mass of C$_{22}$H$_{26}$O$_4$N$_2$ 382.1893).

Example 7: Preparation of Compound 11

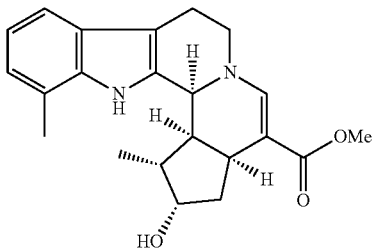

Compound 11

Compound 11 (10.1 mg) was obtained according to the same method as Example 4 with the exception that 7-methyltryptamine (71 mg, 0.40 mmol) was used instead of 6-methoxytryptamine (126 mg, 0.66 mmol) in step 3.

Compound 11 was analyzed by mass spectrometry based on EIMS (electron impact mass spectrometry), and NMR. The results of EIMS and NMR are shown below.

$^1$H-NMR (600 MHz, CDCl$_3$) δ 8.10 (1H, br.s), 7.34 (1H, s), 7.29 (1H, d, J=7.8 Hz), 7.01 (1H, t, J=7.8 Hz), 6.95 (1H, t, J=7.8 Hz), 4.39 (15, br.s), 4.22 (1H, t, J=5.4 Hz), 3.70 (1H, dd, J=13.1, 6.0 Hz), 3.60 (3H, s), 3.44 (1H, ddd, J=13.1, 12.0, 4.5 Hz), 2.95-3.00 (1H, m), 2.88-2.95 (1H, m), 2.74 (1H, dd, J=14.5, 5.6 Hz), 2.47 (3H, s), 2.40-2.44 (1H, m), 2.23 (1H, ddd, J=14.8, 8.2, 0.9 Hz), 2.02-2.10 (1H, m), 1.78 (1H, dt, J=14.8, 5.4 Hz), 1.20 (3H, d, J=7.0 Hz).

$^{13}$C-NMR (150 MHz, CDCl$_3$) δ 168.6, 144.7, 135.3, 133.0, 126.6, 122.6, 120.3, 119.9, 115.6, 109.1, 104.3, 74.5, 52.9, 51.5, 50.6, 44.7, 42.5, 41.6, 31.0, 22.3, 16.8, 12.7.

EIMS m/z (rel. int) 366 [M]$^+$ (100), 348 (41), 305 (80), 293 (91).

HREIMS m/z 366.1968 (Calculated mass of C$_{22}$H$_{26}$O$_3$N$_2$ 366.1943).

Example 8: Preparation of Compound 12

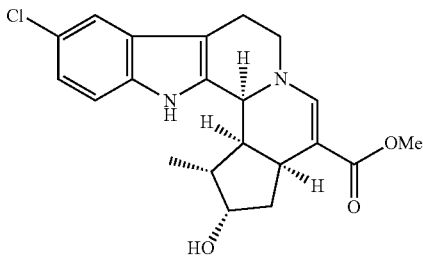

Compound 12

Compound 12 (2.0 mg) was obtained according to the same method as Example 4 with the exception that 5-chlorotryptamine (114 mg, 0.59 mmol) was used instead of 6-methoxytryptamine (126 mg, 0.66 mmol) in step 3.

Compound 12 was analyzed by mass spectrometry based on EIMS (electron impact mass spectrometry), and NMR. The results of EIMS and NMR are shown below.

$^1$H-NMR (00 MHz, CDCl$_3$) δ 8.09 (1H, br.s), 7.38 (1H, d, J=1.9 Hz), 7.31 (1H, d, J=1.0 Hz), 7.20 (1H, d, J=8.6 Hz), 7.08 (1H, dd, J=8.6, 1.9 Hz), 4.37 (1H, br.s), 4.22 (1H, t, J=5.2 Hz), 3.71 (1H, dd, J=13.3, 6.7 Hz), 3.60 (3H, s), 3.42 (1H, ddd, J=13.3, 11.9, 4.6 Hz), 2.92-2.97 (1H, m), 2.84-2.90 (1H, m), 2.74 (1H, dd, J=15.4, 4.6 Hz), 2.36 (1H, ddd, J=9.7, 8.1, 3.7 Hz), 2.23 (1H, ddd, J=14.8, 8.0, 1.2 Hz), 2.01-2.08 (1H, m), 1.79 (1H, dt, J=14.8, 5.2 Hz), 1.17 (3H, d, J=7.0 Hz).

$^{13}$C-NMR (150 MHz, CDCl$_3$) δ 168.4, 144.3, 134.9, 134.1, 128.3, 125.5, 122.2, 117.7, 111.9, 108.5, 104.9, 74.5, 52.7, 51.3, 50.7, 44.8, 42.5, 41.4, 30.8, 22.0, 12.7.

EIMS m/z (rel. int) 388 [M+2]$^+$ (22), 386 [M]$^+$ (99), 368 (69), 327 (71), 313 (100), 289 (68), 204 (71).

HREIMS m/z 386.1369 (Calculated mass of C$_{21}$H$_{23}$O$_3$N$_2$$^{35}$Cl 386.1397).

Example 9: Preparation of Compound 13

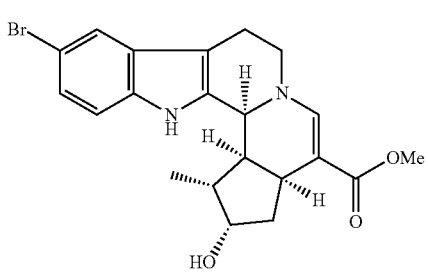

Compound 13

Compound 13 (1.4 mg) was obtained according to the same method as Example 4 with the exception that 5-bromotryptamine (133 mg, 0.56 mmol) was used instead of 6-methoxytryptamine (126 mg, 0.66 mmol) in step 3.

Compound 13 was analyzed by mass spectrometry based on EIMS (electron impact mass spectrometry), and NMR. The results of EIMS and NMR are shown in below.

$^1$H-NMR (600 MHz, CDCl$_3$) δ 8.05 (1H, br.s), 7.55 (1H, d, J=1.8 Hz), 7.31 (1H, s), 7.22 (1H, dd, J=8.5, 1.8 Hz), 7.17 (1H, d, J=8.5 Hz), 4.37 (1H, br.s), 4.22 (1H, t, J=5.1 Hz), 3.71 (1H, dd, J=13.3, 5.8 Hz), 3.60 (3H, s), 3.42 (1H, ddd, J=13.3, 12.0, 4.6 Hz), 2.92-2.98 (1H, m), 2.84-2.90 (1H, m), 2.74 (1H, dd, J=15.4, 4.6 Hz), 2.36 (1H, ddd, J=9.9, 8.3, 3.7 Hz), 2.21 (1H, ddd, J=14.8, 8.1, 0.9 Hz), 2.02-2.09 (1H, m), 1.79 (1H, dt, J=14.8, 5.1 Hz), 1.17 (3H, d, J=7.0 Hz).

$^{13}$C-NMR (150 MHz, CDCl$_3$) δ 168.4, 144.3, 134.8, 134.4, 129.0, 124.7, 120.8, 113.0, 112.4, 108.5, 104.9, 74.4, 52.7, 51.3, 50.7, 44.8, 42.5, 41.4, 30.8, 22.0, 12.7.

EIMS m/z (rel. int) 432 [M+2]$^+$ (72), 430 [M]$^+$ (100), 371 (90), 359 (95), 333 (56), 248 (50).

HREIMS m/z 430.0885 (Calculated mass of C$_{21}$H$_{23}$O$_3$N$_2$$^{79}$Br 430.0892).

Example 10: Preparation of Compound 14

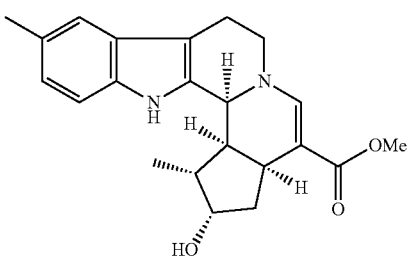

Compound 14

Compound 14 (9.3 mg) was obtained according to the same method as Example 4 with the exception that 5-methyltryptamine (96 mg, 0.55 mmol) was used instead of 6-methoxytryptamine (126 mg, 0.66 mmol) in step 3.

Compound 14 was analyzed by mass spectrometry based on EIMS (electron impact mass spectrometry), and NMR. The results of EIMS and NMR are shown below.

$^1$H-NMR (600 MHz, CDCl$_3$) δ 8.15 (1H, br.d), 7.33 (1H, d, J=0.9 Hz), 7.22 (1H, d, J=1.1 Hz), 7.19 (1H, d, J=8.3 Hz), 6.95 (1H, dd, J=8.3, 1.1 Hz), 4.35 (1H, br.s), 4.21 (1H, t, J=4.7 Hz), 3.69 (1H, dd, J=12.9, 5.9 Hz), 3.59 (3H, s), 3.43 (1H, ddd, J=12.9, 11.9, 4.7 Hz), 2.92-2.97 (1H, m), 2.85-2.92 (1H, m), 2.71 (1H, dd, J=15.2, 4.7 Hz), 2.41 (3H, s), 2.31-2.37 (1H, m), 2.20 (1H, ddd, J=14.7, 7.8, 1.1 Hz), 2.01-2.09 (1H, m), 1.76 (1H, dt, J=14.7, 5.6 Hz), 1.17 (3H, d, J=7.0 Hz).

$^{13}$C-NMR (150 MHz, CDCl$_3$) δ 168.6, 144.7, 134.1, 133.5, 128.9, 127.3, 123.4, 117.7, 110.7, 108.1, 104.2, 74.4, 52.9, 51.5, 50.6, 44.9, 42.5, 41.5, 31.0, 22.2, 21.4, 14.2, 12.8.

EIMS m/z (rel. int) 366 [M]$^+$ (100), 307 (55), 295 (35), 269 (21), 184 (15).

HREIMS m/z 366.1956 (Calculated mass of C$_{22}$H$_{26}$O$_3$N$_2$ 366.1943).

Example 11: Preparation of Compound 15

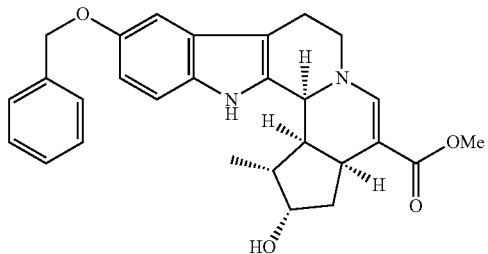

Compound 15

Compound 15 (10.3 mg) was obtained according to the same method as Example 4 with the exception that 5-benzyloxytryptamine (102 mg, 0.38 mmol) instead of 6-methoxytryptamine (126 mg, 0.66 mmol) in step 3.

Compound 15 was analyzed by mass spectrometry based on EIMS (electron impact mass spectrometry), and NMR. The results of EIMS and NMR are shown below.

$^1$H-NMR (600 MHz, CDCl$_3$) δ 8.20 (1H, br.s), 7.45 (2H, dd, J=7.3, 1.1 Hz), 7.36 (2H, t, J=7.3 Hz), 7.33 (1H, d, J=1.0 Hz), 7.29 (1H, t, J=7.3 Hz), 7.20 (1H, d, J=8.7 Hz), 6.97 (1H, d, J=2.3 Hz), 6.87 (1H, dd, J=8.7, 2.3 Hz), 5.07 (2H, s), 4.35 (1H, br.s), 4.20 (1H, t, J=5.0 Hz), 3.69 (1H, dd, J=12.9, 5.8 Hz), 3.60 (3H, s), 3.43 (1H, td, J=12.9, 4.5 Hz), 2.92-2.97 (1H, m), 2.83-2.90 (1H, m), 2.71 (1H, dd, J=15.3, 4.5 Hz), 2.33-2.38 (1H, m), 2.19 (1H, ddd, J=14.7, 9.0, 1.2 Hz), 2.00-2.08 (1H, m), 1.78 (1H, dt, J=14.7, 5.8 Hz), 1.16 (3H, d, J=6.9 Hz).

$^{13}$C-NMR (150 MHz, CDCl$_3$) δ 168.6, 153.4, 144.6, 137.6, 134.3, 131.1, 128.5 (2C), 127.7, 127.5 (3C), 112.4, 111.7, 108.4, 104.3, 101.9, 74.4, 71.0, 52.9, 51.5, 50.6, 44.8, 42.5, 41.5, 30.9, 22.2, 12.8.

EIMS m/z (rel. int) 458 [M]$^+$ (100), 440 (54), 399 (52), 367 (79).

HREIMS m/z 458.2194 (Calculated mass of C$_{28}$H$_{30}$O$_4$N$_2$ 458.2206).

Example 12: Preparation of Compound 16

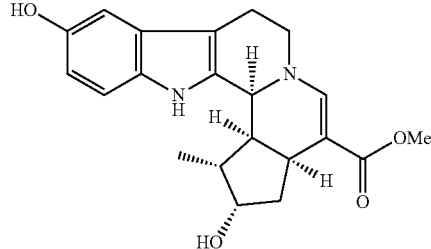

Compound 16

Compound 15 (4.0 mg, 8.72 μmol) was dissolved in methanol (0.5 mL). To the solution was added 20% palladium hydroxide on carbon (1.0 mg), and the mixture was stirred under hydrogen atomosphere (1 atm) at room temperature for 15 hours. The reaction solution was filtered, and solvent of the filtrate was removed under reduced pressure. The residue was subjected to silica gel column chromatography to give compound 16 (2.9 mg, 7.88 μmol) from a fraction eluted with acetonitrile-water (7:3).

Compound 16 was analyzed by mass spectrometry based on EIMS (electron impact mass spectrometry), and NMR. The results of EIMS and NMR are shown below.

$^1$H-NMR (600 MHz, CD$_3$OD) δ 7.45 (1H, d, J=0.6 Hz), 7.15 (1H, d, J=8.7 Hz), 6.76 (1H, d, J=2.1 Hz), 6.62 (1H, dd, J=8.7, 2.1 Hz), 4.42 (1H, br.s), 4.15 (1H, td, J=5.5, 2.2 Hz), 3.77 (1H, dd, J=12.8, 6.0 Hz), 3.60 (3H, s), 3.47 (1H, td, J=12.8, 4.2 Hz), 2.87-2.91 (1H, m), 2.77-2.85 (1H, m), 2.66 (1H, dd, J=15.0, 4.2 Hz), 2.36 (1H, ddd, J=9.5, 8.0, 4.1 Hz), 2.14 (1H, ddd, J=14.3, 7.7, 2.2 Hz), 2.06-2.11 (1H, m), 1.80 (1H, dt, J=14.3, 5.8 Hz), 1.14 (3H, d, J=7.0 Hz).

$^{13}$C-NMR (150 MHz, CD$_3$OD) δ 171.0, 151.4, 147.1, 135.8, 132.8, 129.1, 112.5, 112.0, 108.1, 104.4, 103.0, 74.7, 54.7, 52.7, 51.1, 46.8, 43.1, 42.4, 32.3, 23.5, 13.4.

EIMS m/z (rel. int) 368 [M]$^+$ (100), 351 (15), 309 (48), 297 (27), 271 (18), 186 (11).

HREIMS m/z 368.1753 (Calculated mass of C$_{21}$H$_{24}$O$_4$N$_2$ 368.1736).

Example 13: Preparation of Compound 17

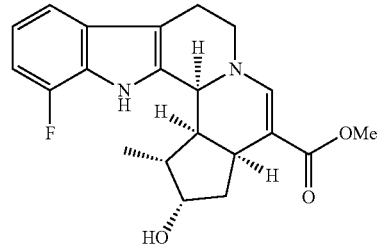

Compound 17

Compound 17 (12.3 mg) was obtained according to the same method as Example 4 with the exception that 6-fluorotryptamine (101 mg, 0.57 mmol) was used instead of 6-methoxytryptamine (126 mg, 0.66 mmol) in step 3.

Compound 17 was analyzed by mass spectrometry based on EIMS (electron impact mass spectrometry), and NMR. The results of EIMS and NMR are shown below.

$^1$H-NMR (600 MHz, CDCl$_3$) δ 8.50 (1H, br.d), 7.32 (1H, s), 7.31 (1H, dd, J=8.6, 5.1 Hz), 6.99 (1H, dd, J=7.6, 2.1 Hz), 6.82 (1H, ddd, J=8.6, 7.3, 2.1 Hz), 4.35 (1H, br.s), 4.21 (1H, t, J=4.9 Hz), 3.70 (1H, dd, J=12.9, 5.9 Hz), 3.59 (3H, s), 3.43 (1H, td, J=12.9, 4.5 Hz), 2.91-2.96 (1H, m), 2.84-2.91 (1H, m), 2.70 (1H, dd, J=15.3, 4.5 Hz), 2.40 (1H, td, J=9.5, 3.5 Hz), 2.20 (1H, ddd, J=14.7, 8.0 Hz), 1.99-2.05 (1H, m), 1.77 (1H, dt, J=14.7, 5.7 Hz), 1.15 (3H, d, J=6.8 Hz).

$^{13}$C-NMR (150 MHz, CDCl$_3$) δ 168.6, 159.8 (d, J=237.3 Hz), 144.6, 135.8 (d, J=12.2 Hz), 133.6 (d, J=2.9 Hz), 123.7, 118.5 (d, J=10.0 Hz), 108.5, 108.1 (d, J=24.4 Hz), 104.6, 97.5 (d, J=25.8 Hz), 74.5, 52.7, 51.4, 50.7, 44.7, 42.4, 41.4, 30.8, 22.1, 12.7.

EIMS m/z (rel. int) 370 [M]$^+$ (100), 311 (76), 297 (53), 273 (35), 188 (40).

HREIMS m/z 370.1685 (Calculated mass of C$_{21}$H$_{23}$O$_3$N$_2$F 370.1693).

Pharmacological Tests

The following are methods and results of pharmacological tests for the example compounds of the present invention.

Experimental Materials (1) Cells

MT2 cells from human adult T-cell leukemia were used. Leukemia cells of human adult T-cell leukemia (ATL) express CD4 and CD25 molecules on the cell surface and are considered to be derived from Treg (Chen S. et al., International Immunology 18:269-277 (2005)). MT2 cells were used in experiments as models of Treg since the cells are CD4 positive, CD25 positive, and FOXP3 positive celles derived from ATL.

(2) Test Samples

The example compounds (compounds 1-17) of the present invention were dissolved in dimethylsulfoxide (DMSO) to prepare each 50 mmol/L solution, which was preserved at −80° C.

Test 1: Measurement of Human IL-10 Amount in Culture Supernatant with ELISA Kit

The amount of IL-10 production in the control and the example compounds was measured to evaluate the inhibitory effect on IL-10 production of the example compounds of the present invention.

(1) MT2 cells are suspended in RPMI1640 medium (hereinafter referred to as "the medium") supplemented with 10% fetal calf serum (FCS) and 1% penicillin/streptomycin (P/S) to give 3×10$^5$ cells/mL suspension, and 1 mL of the suspension was added to each well of a 24-well plate. The test samples (compound 1-7) were diluted 50-fold with medium, and 25.0 μL or 12.5 μL of the diluent was added to each well. The cell cultures were incubated 48±2 hours in a CO$_2$ incubator (under a condition of 37° C., 5 CO$_2$). DMSO was diluted 50-fold with the medium, and 20 μL of the diluent was added to the well to make a control of compounds 1-7. In addition, DMSO was diluted 50-fold with the medium, and 25.0 μL of the diluent was added to the well to make a control of compounds 8-17.

(2) A piece of the cell culture was sampled to count cells with a cell counter (BIO RAD TC-20). The cell culture was centrifuged at 300×g for 5 minutes and the supernatant was collected as a sample for IL-10 measurement. When not measured within a day, it was preserved in a freezer at −80° C.

(3) Human IL-10 ELISA kit II (BD OptEIA) was used on the measurement. The kit contains wells treated with anti-IL-10 antibody (8 wells/strip), Standard/Sample diluent, vials comprising freeze-dried IL-10 Standard (1280 pg/vial), ELISA diluent, 20× Wash Buffer, Detection antibody, Enzyme Concentrate, TMB One Step Substrate Reagent, Stop Solution, and cover sheets.

(4) To a vial containing IL-10 Standard was added 2.3 mL Standard/Sample diluent, and the vial was stood at room temperature for 15 minutes to be dissolved (Standard sample stock solution 1L-10 concentration: 500 pg/mL).

(5) Standard samples in each concentration for making a standard curve were prepared as follows. Firstly, to 300 μL of the medium was added 300 μL of the standard sample stock solution, and the mixture was mixed with a Voltex mixer (250 pg/mL). Next, 300 μL of the standard sample of 250 pg/mL was added to 300 μL of the medium and the mixture was mixed with a Voltex mixer (125 pg/mL). The same procedures were successively repeated to prepare standard solutions of 62.5, 31.25, 15.625, and 7.8125 pg/mL. As 0 pg/mL standard solution, the medium was used.

(6) A kit containing wells treated with anti-IL-10 antibody (8 wells/strip) was warmed to room temperature and 50 μL of ELISA diluent in the kit was added into each well.

(7) To each well containing ELISA diluent, 100 μL of the standard samples of each concentration and each test sample (diluded 50-100 fold with medium) were added.

(8) After the wells were sealed with a cover sheet and gently tapped, they were left at room temperature for 2 hours.

(9) 20× Wash Buffer was diluted 20-fold with water to prepare 1× Wash Buffer.

(10) After the reaction was done for 2 hours, the solutions in each well were aspirated and washed 5 times with 300 μL of 1× Wash Buffer.

(11) After Enzyme Concentrate (4 μL per 8 wells) was added to Detection antibody (1 ml per 8 wells), the solution was mixed by a Vortex mixer and then a necessary amount of Working Detector was prepared.

(12) 100 μL of Working Detector was added to each well, covered with a cover sheet, and the wells were left at room temperature for an hour.

(13) After the reaction was done for an hour, the solutions in wells were aspirated and washed 7 times with 300 μL of 1× Wash Buffer.

(14) 100 μL of TMB One Step Substrate Reagent was added to the wells and the wells were left in the dark for 30 min.

(15) Within 30 min after 50 μL of Stop solution was added to the wells, the absorbance at 470 nm which was subtracted by the absorbance at 570 nm as a background was measured with a microplate reader (Thermo Scientific; Varioskan Flash).

(16) A regression line (a standard curve) was made from the absorbance of the standard samples of each concentration using Microsoft Excel 2013 to calculate the evaluation values of the control and the test samples treated with each compound from the standard curve. The experiments were conducted in n=3, and the values of each group were shown as average and standard deviation values.

Through the evaluation of the example compounds of the present invention in the above pharmacological tests, has been found that the compounds of the present invention exhibit the inhibitory effect on IL-10 production. The IL-10 production inhibitory activity of the control and each compound, and inhibition rate (%) of each compound against the control are shown in Table 1 below.

TABLE 1

Inhibitory effect of example compounds on IL-10 production from MT2 cells

| Compound number and concentration for addition | IL-10 (ng/$10^6$ cells) ± standard deviate (n = 3) | % against control |
|---|---|---|
| Control (DMSO) | 18.5 ± 0.6 | 100.0% |
| Compound 1 10 μmol/L | 10.4 ± 0.2 | 56.1% |
| Compound 1 20 μmol/L | 7.3 ± 0.3 | 39.3% |
| Compound 2 10 μmol/L | 14.5 ± 0.3 | 78.5% |
| Compound 2 20 μmol/L | 11.0 ± 0.2 | 59.3% |
| Compound 3 10 μmol/L | 14.8 ± 0.3 | 80.0% |
| Compound 3 20 μmol/L | 11.8 ± 0.3 | 63.7% |
| Compound 4 10 μmol/L | 8.0 ± 0.2 | 42.9% |
| Compound 4 20 μmol/L | 4.3 ± 0.5 | 23.0% |
| Compound 5 10 μmol/L | 19.7 ± 0.2 | 106.3% |
| Compound 5 20 μmol/L | 14.9 ± 0.4 | 80.5% |
| Compound 6 10 μmol/L | 17.6 ± 0.7 | 95.2% |
| Compound 6 20 μmol/L | 15.2 ± 0.4 | 81.8% |
| Compound 7 10 μmol/L | 17.9 ± 0.6 | 96.5% |
| Compound 7 20 μmol/L | 15.4 ± 0.4 | 83.1% |
| Control (DMSO) | 18.5 ± 0.6 | 100.0% |
| Compound 8 12.5 μmol/L | 15.5 ± 1.2 | 94.6% |
| Compound 8 25.0 μmol/L | 7.9 ± 0.4 | 48.4% |
| Compound 9 12.5 μmol/L | 11.1 ± 1.3 | 67.7% |
| Compound 9 25.0 μmol/L | 6.1 ± 1.3 | 37.5% |
| Control (DMSO) | 9.4 ± 0.2 | 100.0% |
| Compound 10 12.5 μmol/L | 8.8 ± 0.4 | 93.5% |
| Compound 10 25.0 μmol/L | 5.6 ± 0.3 | 59.6% |
| Compound 11 12.5 μmol/L | 7.4 ± 0.2 | 78.2% |
| Compound 11 25.0 μmol/L | 5.6 ± 0.3 | 55.4% |
| Compound 12 12.5 μmol/L | 7.1 ± 0.2 | 75.7% |
| Compound 12 25.0 μmol/L | 4.8 ± 0.3 | 50.9% |
| Compound 13 12.5 μmol/L | 7.7 ± 0.6 | 81.2% |
| Compound 13 25.0 μmol/L | 4.2 ± 0.2 | 44.0% |
| Control (DMSO) | 11.0 ± 1.2 | 100.0% |
| Compound 14 12.5 μmol/L | 7.4 ± 0.3 | 67.7% |
| Compound 14 25.0 μmol/L | 4.3 ± 1.0 | 39.2% |
| Compound 15 12.5 μmol/L | 6.5 ± 0.2 | 59.3% |
| Compound 15 25.0 μmol/L | 0.6 ± 0.4 | 5.1% |
| Compound 16 12.5 μmol/L | 9.8 ± 0.3 | 88.90% |
| Compound 16 25.0 μmol/L | 8.6 ± 0.1 | 77.90% |
| Compound 17 12.5 μmol/L | 7.0 ± 0.2 | 64.20% |
| Compound 17 25.0 μmol/L | 6.0 ± 0.2 | 54.20% |

Example 2: Intracellular Staining with Anti-CTLA-4 Antibody Labeled with Antibody-Fluorescence and Measurement by Flow Cytometry According to the following procedures, the expression levels of CTLA-4 were measured to evaluate the immune checkpoint inhibitory effect of compounds 1, 2, 4, and 8-17 which have especially potent inhibitory effect among the above compounds which exhibited the IL-10 inhibitory effect in Test 1.

(1) MT2 cells were suspended in RPMI1640 medium (hereinafter referred to as "the medium") supplemented with 10% fetal calf serum (FCS) and 1° penicillin/streptomycin (P/S) to give $3\times10^5$ cells/mL suspension and 3 mL of the suspension was added to each well of a 6-well plate. To each well were added 0.6 or 1.2 μL of the test compound solutions (compounds 1, 2, and 4), 0.75 or 1.5 μL of the test compound solution (compound 9), and 1.5 μL of the test compound solutions (compounds 8 and 10-17), and the cell cultures were incubated in a $CO_2$ gas incubator (under 37° C., 5% $CO_2$) and cultured for 48±2 hours. As a control of compound 1, 2 and 4, only 1.2 μL of DMSO was added to the well. In addition, as a control of compound 8-17, only 1.5 μL of DMSO was added to the well.

(2) A piece of the cell culture was sampled to count cells with a cell counter (BIO RAD TC-20). The cell culture was centrifuged at 300×g for 5 min, and the supernatant was removed. The residue was suspended in phosphate buffered saline (supplemented with 1% bovine serum albumin (BSA), without calcium and magnesium) (1% BSA/PBS) to adjust the concentration of cells to $5\text{-}10\times10^6$ cells/mL.

(3) To 5 ml tube, each 50 μL of the cell suspension was added.

(4) Foxp3/Transcription Factor Fix/Perm Concentrate (4×) (Cat. No. TNB-1020-L050) (Solution A) in FOXP3/Transcription Factor Staining kit (TONBO biosciences) was diluted with Foxp3/Transcription Factor Fix/Perm Diluent (1×) (Cat. No. TNB-1022-L160) (for dilution of Solution A) to prepare 1× Solution A.

(5) 1 mL of 1× Solution A was added to each tube and mixed by gentle pipetting. Subsequently, it was left at room temperature for 30 min, centrifuged at 300×g for min, and the supernatant was discarded.

(6) Flow Cytometry Perm Buffer (10×) (Cat. No. TNB-1213-L150) (Solution B) in the kit was diluted 10-fold with water to prepare 1× Solution B.

(7) 2 mL of 1× Solution B was added to the tube and centrifuged at 300×g for 5 min. The supernatant was discarded. 2 μL of 2% normal mouse serum/PBS was added to the tube and the tube was gently pipetted. Subsequently, it was left at room temperature for 15 min.

(8) In the CTLA-4 measurement, 20 μL of anti-CTLA-4 antibody (BECKMAN COULTER, CD152-PE clone BN13I M2282) or mouse IgG2a (BECKMAN COULTER, IgG2a (Mouse)-PE A09142) for the control was added to the tube and the tube was gently stirred. Subsequently, it was left in the dark at room temperature for 30 min, and 2 mL of the 1× Solution B was added thereto, the mixture was centrifuged at 300×g for 5 min, and the supernatant was discarded. 2 mL of the 1× Solution B was added to the tube again, the mixture was centrifuged at 300×g for 5 min, and the supernatant was discarded.

(9) Within 2 hours after the solution in the tube was suspended in 0.5 mL of 1% BSA/PBS, and the fluorescence at 577 nm was measured with 488 nm excitation with a flow cytometer (Sony: Cell Sorter SH800). The results were analyzed with software, FlowJo (Tree Star Inc.). The mean peak fluorescence intensity (MFI) of CTLA-4 and mean peak fluorescence intensity of isotype control IgG2a were calculated from histgrams of the measured fluorescence intensity and number of cells, and mean fluorescence intensity of IgG2a was subtracted from that of CTLA-4. Experiments were conducted in n=3, and the average values were shown.

Compounds 1, 2, and 4 (10 μmol/L and 20 μmol/L), compound 9 (12.5 μmol/L and 25.0 μmol/L), and compounds 8 and 10-17 (25.0 μmol/L) of the present invention were evaluated in the above pharmacological tests, and it has been found that compounds 1, 4, and 8-17, especially compounds 1, 15, and 17 of the present invention exhibit the inhibitory effect on CTLA-4 expression. The CTLA-4 expression inhibitory activity of the control and each compound, and the inhibition rate (%) against the control are shown in Table 2 below.

TABLE 2

Inhibitory effect of test compounds on CTLA-4 expression from MT2 cells

| Compound number and concentration | Peak MFI of CTLA-4 | % against control |
|---|---|---|
| Control (DMSO) | 800.5 | 100.0% |
| Compound 1 10 μmol/L | 608.5 | 76.0% |
| Compound 1 20 μmol/L | 358.5 | 44.8% |
| Control (DMSO) | 1138.0 | 100.0% |
| Compound 2 10 μmol/L | 1225.0 | 107.6% |
| Compound 2 20 μmol/L | 1139.5 | 100.1% |
| Control (DMSO) | 852.0 | 100.0% |
| Compound 4 10 μmol/L | 796.0 | 93.4% |
| Compound 4 20 μmol/L | 621.0 | 72.9% |
| Control (DMSO) | 1020 | 100.0% |
| Compound 9 12.5 μmol/L | 778 | 76.3% |
| Compound 9 25.0 μmol/L | 539 | 52.8% |
| Control (DMSO) | 723 | 100.0% |
| Compound 8 25.0 μmol/L | 361 | 50.0% |
| Control (DMSO) | 1011 | 100.0% |
| Compound 10 25.0 μmol/L | 570 | 56.3% |
| Compound 11 25.0 μmol/L | 602 | 59.5% |
| Control (DMSO) | 848 | 100.0% |
| Compound 12 25.0 μmol/L | 485 | 57.2% |
| Compound 13 25.0 μmol/L | 775 | 91.6% |
| Compound 14 25.0 μmol/L | 450 | 53.0% |
| Control (DMSO) | 753 | 100.0% |
| Compound 15 25.0 μmol/L | 284 | 37.7% |
| Compound 16 25.0 μmol/L | 529 | 70.3% |
| Compound 17 25.0 μmol/L | 339 | 45.0% |

From the above results, it was confirmed that the compounds of the present invention have CTLA-4 inhibitory activity, i.e., immune checkpoint inhibitory activity.

INDUSTRIAL APPLICABILITY

The compounds of the present invention have inhibitory effect on CTLA-4 expression and IL-10 production, and are useful for prevention and/or treatment of diseases caused by immune checkpoints, especially cancer. In addition, they are also useful as vaccine adjuvants.

The invention claimed is:
1. A compound of formula (I):

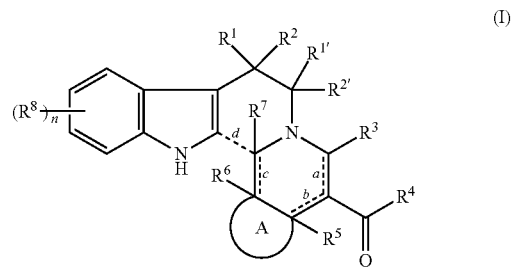

or a pharmaceutically acceptable salt thereof
wherein
a, b, and c respectively designate bonds ==== that denote a single bond or a double bond, and d designates - - - - that denotes an absent bond or a single bond,
wherein when the a is a double bond, the b is a single bond; when the b is a double bond, the a is a single bond and $R^5$ is absent; when the c is a double bond, $R^6$ is absent; and when the c is a double bond and the d is a single bond, $R^6$ and $R^7$ are absent;

A is a $C_{3-6}$ cycloalkyl ring, $C_{3-6}$ cycloalkenyl ring, or 5- or 6-membered monocyclic heterocycle, wherein the $C_{3-6}$ cycloalkyl ring, the $C_{3-6}$ cycloalkenyl ring, and the 5- or 6-membered monocyclic heterocycle each are independently and optionally substituted with one or more of the same or different groups selected from the group consisting of halogen, hydroxy, oxo, amino, nitro, mono- or di-$C_{1-6}$ alkyl-amino, $C_{1-4}$ acyl, $C_{1-6}$ alkyl, $C_{1-6}$ haloalkyl, $C_{1-6}$ hydroxyalkyl, $C_{1-6}$ alkoxy, and $C_{1-6}$ haloalkoxy;

$R^1$, $R^{1'}$, $R^2$, $R^{2'}$, and $R^3$ each independently represent hydrogen, halogen, hydroxy, amino, nitro, mono- or di-$C_{1-6}$ alkyl-amino, $C_{1-6}$ alkyl, $C_{1-6}$ haloalkyl, $C_{1-6}$ hydroxyalkyl, $C_{1-6}$ alkoxy, or $C_{1-6}$ haloalkoxy;

$R^4$ represents hydrogen, halogen, hydroxy, amino, mono- or di-$C_{16}$ alkyl-amino, $C_{1-6}$ alkyl, $C_{2-6}$ alkenyl, $C_{2-6}$ alkynyl, $C_{1-6}$ alkoxy, $C_{3-6}$ cycloalkyl, 3- to 6-membered heterocycloalkyl, $C_{6-10}$ aryl, or 6- to 10-membered heteroaryl,
wherein the $C_{1-6}$ alkyl, the $C_{2-6}$ alkenyl, the $C_{2-6}$ alkynyl, the $C_{1-6}$ alkoxy, the $C_{3-6}$ cycloalkyl, the 3- to 6-membered heterocycloalkyl, the $C_{6-10}$ aryl, and the 6- to 10-membered heteroaryl each are optionally and independently substituted with one or more of the same or different groups selected from the group consisting of halogen, hydroxy, amino, nitro, mono- or di-$C_{1-6}$ alkylamino, $C_{1-4}$ acyl, $C_{1-6}$ alkyl, $C_{1-6}$ haloalkyl, $C_{1-6}$ hydroxyalkyl, $C_{1-6}$ alkoxy, and $C_{1-6}$ haloalkoxy, at any substitutable position;

$R^5$, $R^6$, and $R^7$ each independently represent hydrogen, halogen, hydroxy, $C_{1-3}$ alkyl, $C_{1-3}$ haloalkyl, $C_{1-3}$ hydroxyalkyl, $C_{1-3}$ alkoxy, or $C_{1-3}$ haloalkoxy;

$(R^8)_n$ each independently represent halogen, hydroxy, amino, nitro, mono- or di-$C_{1-6}$ alkyl-amino, $C_{1-6}$ alkyl, $C_{2-6}$ alkenyl, $C_{2-6}$ alkynyl, $C_{1-6}$ alkoxy, benzyloxy, C$_{3-6}$ cycloalkyl, 3- to 6-membered heterocycloalkyl, C$_{6-10}$ aryl, or 6- to 10-membered heteroaryl,
wherein the C$_{1-6}$ alkyl, the C$_{2-6}$ alkenyl, the C$_{2-6}$ alkynyl, the C$_{1-6}$ alkoxy, the C$_{3-6}$ cycloalkyl, the 3- to 6-membered heterocycloalkyl, the C$_{6-10}$ aryl, and the 6- to 10-membered heteroaryl are each optionally and independently substituted with one or more of the same or different groups selected from the group consisting of halogen, hydroxy, amino, nitro, mono- or di-C$_{1-6}$ alkyl-amino, C$_{1-4}$ acyl, C$_{1-6}$ alkyl, C$_{1-6}$ haloalkyl, C$_{1-6}$ hydroxyalkyl, C$_{1-6}$ alkoxy, and C$_{1-6}$ haloalkoxy, at any substitutable position; and
n is 1-4.

2. The compound of claim 1 or a pharmaceutically acceptable salt thereof, wherein the a is not a double bond.

3. The compound of claim 1 or a pharmaceutically acceptable salt thereof, wherein R$^4$ represents hydrogen, hydroxy, amino, mono- or di-C$_{1-6}$ alkyl-amino, C$_{1-6}$ alkyl, C$_{1-6}$ haloalkyl, C$_{1-6}$ hydroxyalkyl, C$_{1-6}$ alkoxy, or C$_{1-6}$ haloalkoxy.

4. The compound of claim 1 or a pharmaceutically acceptable salt thereof, wherein (R$^8$)$_n$ each independently represent halogen, hydroxy, amino, mono- or di-C$_{1-6}$ alkyl-amino, C$_{1-6}$ alkyl, C$_{1-6}$ haloalkyl, C$_{1-6}$ hydroxyalkyl, C$_{1-6}$ alkoxy, benzyloxy, or C$_{1-6}$ haloalkoxy.

5. The compound of claim 1 or a pharmaceutically acceptable salt thereof, wherein the A is a C$_{5-6}$ cycloalkyl ring, C$_{5-6}$ cycloalkenyl ring, or 5- or 6-membered saturated monocyclic heterocycle,
wherein the C$_{5-6}$ cycloalkyl ring, the C$_{5-6}$ cycloalkenyl ring, and the 5- or 6-membered saturated monocyclic heterocycle may be independently substituted with one or more of the same or different groups selected from the group consisting of hydroxy, oxo, C$_{1-6}$ alkyl, C$_{1-6}$ haloalkyl, C$_{1-6}$ hydroxyalkyl, C$_{1-6}$ alkoxy, and C$_{1-6}$ haloalkoxy, at any substitutable position.

6. The compound of claim 1 or a pharmaceutically acceptable salt thereof, wherein the A represents a group that is selected from the group consisting of:

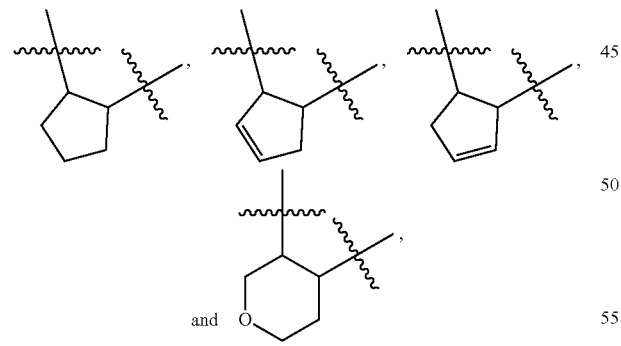

which may be independently substituted with one or more of the same or different groups selected from the group consisting of hydroxy, oxo, C$_{1-3}$ alkyl, C$_{1-3}$ hydroxyalkyl, and C$_{1-3}$ alkoxy, at any substitutable position.

7. The compound of claim 1 or a pharmaceutically acceptable salt thereof, wherein R$^5$, R$^6$, and R$^7$ each independently represent hydrogen or hydroxy.

8. The compound of claim 1 or a pharmaceutically acceptable salt thereof, wherein R$^1$, R$^{1'}$, R$^2$, and R$^{2'}$ represent hydrogen.

9. The compound of claim 1 or a pharmaceutically acceptable salt thereof, wherein R$^3$ represents a C$_{1-6}$ alkyl, C$_{1-6}$ haloalkyl, C$_{1-6}$ hydroxyalkyl, C$_{1-6}$ alkoxy, or C$_{1-6}$ haloalkoxy.

10. A pharmaceutical composition comprising the compound or pharmaceutically acceptable salt thereof of claim 1, and a pharmaceutically acceptable carrier.

11. A compound selected from the group consisting of:

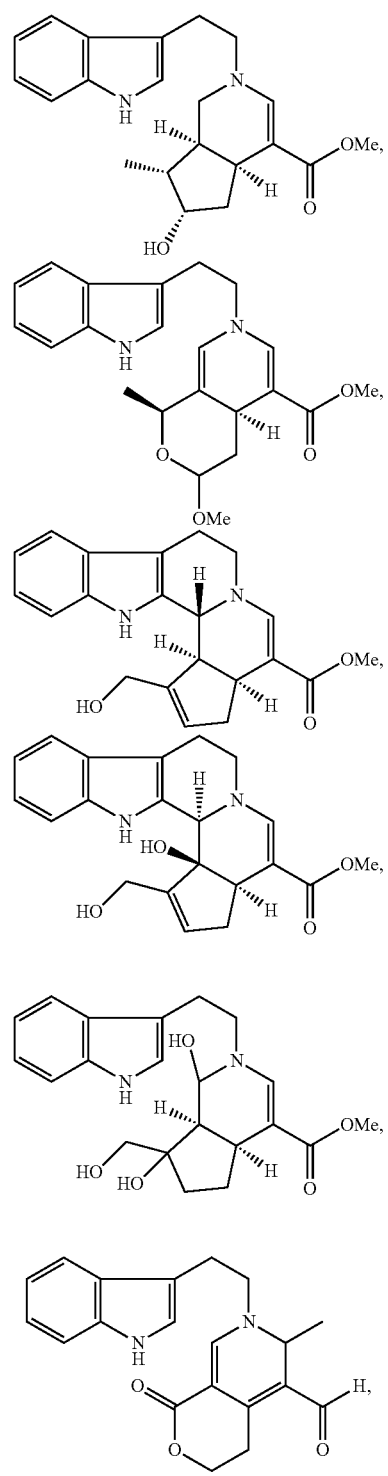

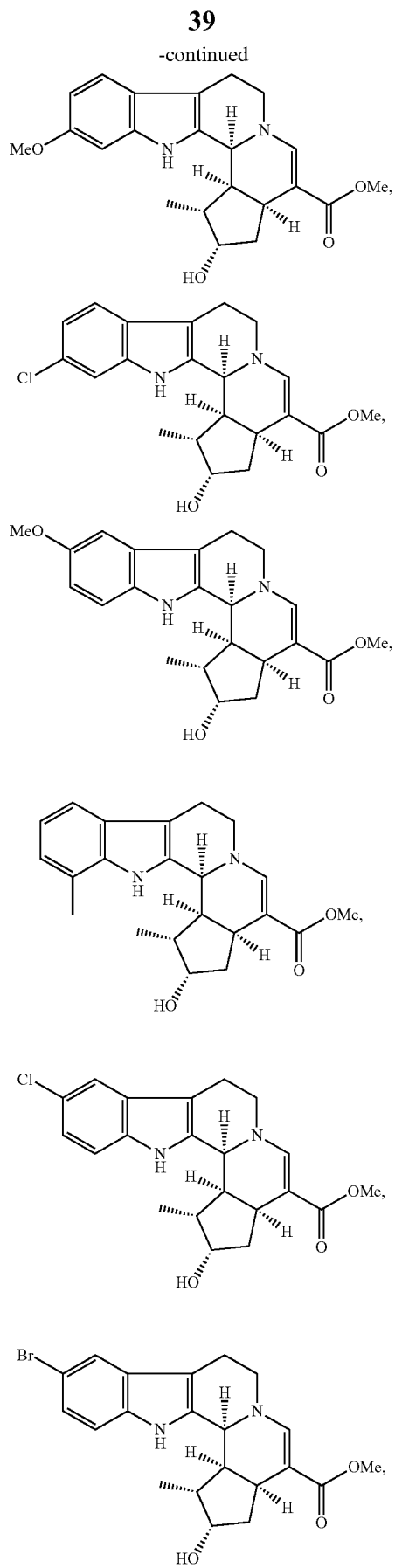

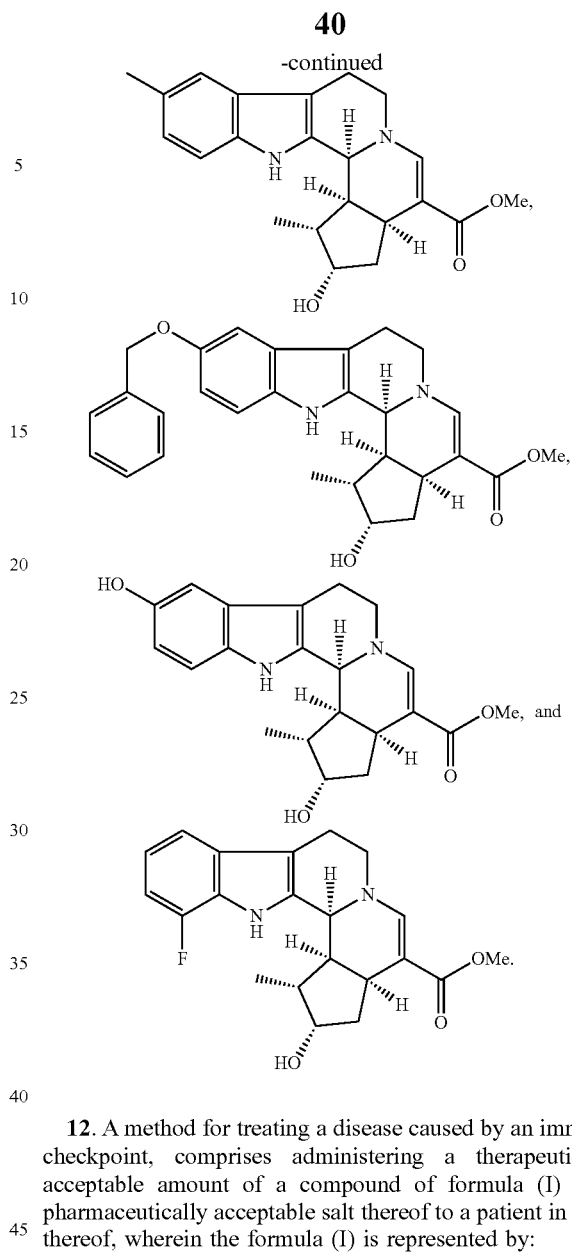

12. A method for treating a disease caused by an immune checkpoint, comprises administering a therapeutically acceptable amount of a compound of formula (I) or a pharmaceutically acceptable salt thereof to a patient in need thereof, wherein the formula (I) is represented by:

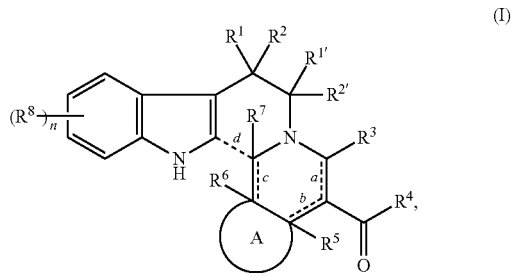

where a, b, and c respectively designate bonds ==== that denote a single bond or a double bond, and d designates - - - - that denotes an absent bond or a single bond,
wherein when the a is a double bond, the b is a single bond; when the b is a double bond, the a is a single bond and $R^5$ is absent; when the c is a double bond, $R^6$ is absent; and when the c is a double bond and the d is a single bond, $R^6$ and $R^7$ are absent;

A is a $C_{3-6}$ cycloalkyl ring, $C_{3-6}$ cycloalkenyl ring, or 5- or 6-membered monocyclic heterocycle, wherein the $C_{3-6}$ cycloalkyl ring, the $C_{3-6}$ cycloalkenyl ring, and the 5- or 6-membered monocyclic heterocycle each may be independently and optionally substituted with one or more of the same or different groups selected from the group consisting of halogen, hydroxy, oxo, amino, nitro, mono- or di-$C_{1-6}$ alkyl-amino, $C_{1-4}$ acyl, $C_{1-6}$ alkyl, $C_{1-6}$ haloalkyl, $C_{1-6}$ hydroxyalkyl, $C_{1-6}$ alkoxy, and $C_{1-6}$ haloalkoxy;

$R^1$, $R^{1'}$, $R^2$, $R^{2'}$, and $R^3$ each independently represent hydrogen, halogen, hydroxy, amino, nitro, mono- or di-$C_{1-6}$ alkyl-amino, $C_{1-6}$ alkyl, $C_{1-6}$ haloalkyl, $C_{1-6}$ hydroxyalkyl, $C_{1-6}$ alkoxy, or $C_{1-6}$ haloalkoxy;

$R^4$ represents hydrogen, halogen, hydroxy, amino, mono- or di-$C_{1-6}$ alkyl-amino, $C_{1-6}$ alkyl, $C_{2-6}$ alkenyl, $C_{2-6}$ alkynyl, $C_{1-6}$ alkoxy, $C_{3-6}$ cycloalkyl, 3- to 6-membered heterocycloalkyl, $C_{6-10}$ aryl, or 6- to 10-membered heteroaryl, wherein the $C_{1-6}$ alkyl, the $C_{2-6}$ alkenyl, the $C_{2-6}$ alkynyl, the $C_{1-6}$ alkoxy, the $C_{3-6}$ cycloalkyl, the 3- to 6-membered heterocycloalkyl, the $C_{6-10}$ aryl, and the 6- to 10-membered heteroaryl may be optionally and independently substituted with one or more of the same or different groups selected from the group consisting of halogen, hydroxy, amino, nitro, mono- or di-$C_{1-6}$ alkylamino, $C_{1-4}$ acyl, $C_{1-6}$ alkyl, $C_{1-6}$ haloalkyl, $C_{1-6}$ hydroxyalkyl, $C_{1-6}$ alkoxy, and $C_{1-6}$ haloalkoxy;

$R^5$, $R^6$, and $R^7$ each independently represent hydrogen, halogen, hydroxy, $C_{1-3}$ alkyl, $C_{1-3}$ haloalkyl, $C_{1-3}$ hydroxyalkyl, $C_{1-3}$ alkoxy, or $C_{1-3}$ haloalkoxy;

$(R^8)_n$ each independently represent hydrogen, halogen, hydroxy, amino, nitro, mono- or di-$C_{1-6}$ alkyl-amino, $C_{1-6}$ alkyl, $C_{2-6}$ alkenyl, $C_{2-6}$ alkynyl, $C_{1-6}$ alkoxy, benzyloxy, $C_{3-6}$ cycloalkyl, 3- to 6-membered heterocycloalkyl, $C_{6-10}$ aryl, or 6- to 10-membered heteroaryl, wherein the $C_{1-6}$ alkyl, the $C_{2-6}$ alkenyl, the $C_{2-6}$ alkynyl, the $C_{1-6}$ alkoxy, the $C_{3-6}$ cycloalkyl, the 3- to 6-membered heterocycloalkyl, the $C_{6-10}$ aryl, and the 6- to 10-membered heteroaryl are each optionally and independently substituted with one or more of the same or different groups selected from the group consisting of halogen, hydroxy, amino, nitro, mono- or di-$C_{1-6}$ alkyl-amino, $C_{1-4}$ acyl, $C_{1-6}$ alkyl, $C_{1-6}$ haloalkyl, $C_{1-6}$ hydroxyalkyl, $C_{1-6}$ alkoxy, and $C_{1-6}$ haloalkoxy; and n is 1-4.

13. The method of claim 12, wherein the immune checkpoint is CTLA-4.

14. The method of claim 12, wherein the disease is a cancer.

15. The method of claim 14, wherein the cancer is malignant melanoma, glioblastoma, lung cancer, gastric cancer, colorectal cancer, liver cancer, pancreatic cancer, renal cancer, adrenal cancer, biliary tract cancer, esophageal cancer, pharyngeal cancer, laryngeal cancer, oral cancer, bladder cancer, tongue cancer, thyroid cancer, skin cancer, breast cancer, prostate cancer, testicular cancer, uterine cancer, cervical cancer, ovarian cancer, osteosarcoma, chondrosarcoma, rhabdomyosarcoma, leiomyosarcoma, leukemia comprising adult T-cell leukemia, malignant lymphoma, or multiple myeloma.

16. The method of claim 12, wherein the therapeutically acceptable amount of the compound of formula (I) or pharmaceutically acceptable salt thereof inhibits the immune checkpoint.

17. The method of claim 16, wherein the immune checkpoint is CTLA-4.

18. The method of claim 12, wherein the compound of formula (I) or pharmaceutically acceptable salt thereof is administered in combination with a vaccine.

* * * * *